United States Patent [19]
Primi

[11] Patent Number: 5,891,623
[45] Date of Patent: Apr. 6, 1999

[54] DIAGNOSIS AND TREATMENT OF AIDS ONSET

[75] Inventor: Daniele Primi, Brescia, Italy

[73] Assignee: Consorzio per le Biotecnologie, Brescia, Italy

[21] Appl. No.: 320,306

[22] Filed: Oct. 6, 1994

Related U.S. Application Data

[62] Division of Ser. No. 973,485, Nov. 9, 1992, abandoned.
[51] Int. Cl.$^6$ .............................. C12P 1/70; G01N 33/53; G01N 33/567
[52] U.S. Cl. ................................. 435/5; 435/7.1
[58] Field of Search ......................... 435/5, 7.1

[56] References Cited

U.S. PATENT DOCUMENTS 4,886,743  12/1989  Hood et al. ................................. 435/5

OTHER PUBLICATIONS

Acha–Orbea et al., Nature 350:207–211 (1991).
Bahadoran et al., Eur. J. Immun. 23(8):2041–2044 (1993).
Boldt–Houle et al., J. Leuk. Biol. 54(5):486–491 (1993).
Boyer et al., Clin. Exp. Immun. 92(3):437–441 (1993).
Brinchmann et al., J. of Vir. 66(10):5924–5928 (1992).
Chase, "Researchers Offer New Theories To Unravel Mysteries of AIDS," The Wall Street Journal, Aug. 4, 1992.
Choi et al., Nature 350:203–207 (1991).
Clarke et al., "Improved Immunogenicity of a Peptide Epitope After Fusion to Hepatitis B Core Protein", Nature, vol. 330, pp. 381–384. (1987).
Dadaglio et al., Int. Conf. AIDS 9(1):203 (1993).
Davis et al., "Antibody and HIV–1 gp120 Recognition of CD4 Undermines the Concept of Mimicry Between Antibodies and Receptors," Nature 358:76–79(1992).
Deusch et al., "Biased T Cell Receptor Vβ Repertoire of Peripheral Blood Derived and Intestinal CD+ T Cells in HIV Disease," Article No. ThA 1539, p. Th72, vol. 1, VIII International Conference on AIDS/III STD World Conference, Amsterdam, the Netherlands. 19–24 Jul. 1992.
Dwyer et al., 55th Meeting Am. Cell. Rheum. Arth. 34(Suppl):S38 (1991).
Gorochov et al., "Conservation of the TCR–V–Beta Chains Repertoire in CD4+ T Cells During Progression of HIV Infection," Article No. ThA 1541, p. Th72, vol. 1, VIII International Conference on AIDS/III STD World Congress, Amsterdam, The Netherlands. 19–24 Jul. 1994.
Haughn, C. Maroun and M. Julius, "Death of Mature T Cells by Separate Ligation of CD4 and the T Cell Receptor for Antigen", Nature, pp. 286–289, vol. 252, 19 Apr., 1991.
Hodars et al., Int. Conf. AIDS 8(1):pTh72 (1992).
Hodars et al., "T Cell Receptor V Gene Expression on CD4 and CD8 Peripheral T Cells From HIV Patients," Article No. ThA 1540, p. Th72, vol. 1, VIII International Conference on AIDS/III STD World Congress, Amsterdam, The Netherlands. 19–24 Jul. 1992.

Hügin et al., "A Virus–Encoded 'Superantigen' in a Retrovirus–Induced Immunodeficiency Syndrome of Mice," Science 252:424–427 (1991).
Imberti et al., "European Biotechnology Today," Malarasi et al., ed. pp. 267–273 (1992).
Imberti et al., Science 254:860–862 (1991).
Kion et al., "Anti–HIV and Anti–Anti–MHC Antibodies in Alloimmune and Autoimmune Mice," Science 253:1138–1140 (1991).
Laurence et al., Nature 358:255–259 (1992).
Laurence et al., "HIV–1 Acts As A Superantigen: TCR Vβ Expression Regulates HIV Replication," Article No. ThA 1538, p. Th72, vol. 1, VIII International Conference on AIDS/III STD World Congress, Amsterdam, The Netherlands. 19–24 Jul. 1992.
Marx, "Autoimmunity Explored in AIDS Pathology," Science 254:799 (1991).
Marx, "Clue Found to T Cell Loss in AIDS," Science 254:798–800 (1991).
Milich et al., A Single 10–Residue Pre–S(1) Peptide Can Prim T Cell Help for Antibody Production to Multiple Epitopes Within the Pre–S(1), Pre–S(2), and S Regions of HBsAg.

(List continued on next page.)

Primary Examiner—Lynette F. Smith
Attorney, Agent, or Firm—Popovich & Wiles, P.A.

[57] ABSTRACT

The invention provides assays for the presence or absence of CD4+ T cell subpopulations carrying particular Vβ components of the T cell receptor (TCR-Vβ) in persons infected with HIV, including amplification of mRNA from T cells with primers specific to each TCR-Vβ to detect the presence or absence of each TCR-Vβ in a sample and primers for use in such amplification assays are disclosed. The invention also provides assays of antibody-containing fluids of a person infected with HIV to determine the immunodeficiency where the fluid is suspected to contain an antibody having a paratope specific to an epitope on a TCR-Vβ. The invention also provides a binding agent specific to a paratope where the paratope is specific to an epitope on a TCR-Vβ. The invention also provides a method of assay of the fluids of a person infected with HIV to determine the immunodeficiency of the person which utilizes a binding agent specific to complexes containing anti-TCR-Vβ antibody bound to TCR-Vβ. The invention also provides a method of treatment of a person infected with HIV to attenuate or avert immunodeficiency which utilize a binding agent that is homologous with an epitope on TCR-Vβ. The invention also provides a method of treatment of a person infected with HIV to attenuate or avert immunodeficiency which involves removing an antibody capable of binding to an epitope on TCR-Vβ from the blood of a person infected with HIV. Finally, the invention provides a method of vaccination of a person infected or at risk for infection with HIV which raises antiidiotypic antibodies specific to free antibodies containing a paratope specific to an epitope on a TCR-Vβ.

6 Claims, 9 Drawing Sheets

OTHER PUBLICATIONS

Moretta et al., "Superantigens in HIV Infection: Expansion or Deletion of T Cell Subsets Expressing Certain Vβs," Orbetello (GR), 13–17 Jun. 1992.

Neurath et al., "Hepatitis B Virus Surface Antigen (HBsAg) as Carrier for Synthetic Peptides Having an Attached Hydrophobic Tail", Molecular Immunology, vol. 26, pp. 53–62. (1989).

Newell et al., "Death of Mature T Cells by Separate Ligation of CD4 and the T Cell Receptor for Antigen," Nature 347:286–289 (1990).

Pantaleo et al., Int. Conf. AIDS, Article No. ThA 1536 p. Th71(1992).

Posnett et al., AIDS 7(5):625–31 (1993).

Soudeyns et al., Sem. Immunol. 5(3):175–185 (1993).

Stevenson et al., J. Vir. 61(12):3741–3748 (1987).

Tunnacliffe et al., PNAS 82:5068–5072 (1985).

Van Brunt, "T Cell Files To Sell CD4 Test," BioWorld Today, p. 2, Oct. 22, 1992.

Van Dongen et al., Clin. Chim. Acta. 198:1–92 (1991).

Wilson et al., "Positive Selection of the Vβ 5 TCR Gene Product in HIV Infected Individuals," Article No. ThA 1537, p. Th72, vol. 1, VIII International Conference on AIDS/III STD World Congress, Amsterdam, The Netherlands. 19–24 Jul. 1992.

Winckur et al., "The Hepatitus A Virus Polyprotein Expressed by a Recombinant Vaccinia Virus Undergoes Protcolytic Processing and Assembly into Virus–like Particles", Journal of Virulogy, vol. 65, pp. 5029–5036. (1991).

Minneapolis Star Tribune, "Key Immune Cell May Slow Aids," Jul. 23, 1992.

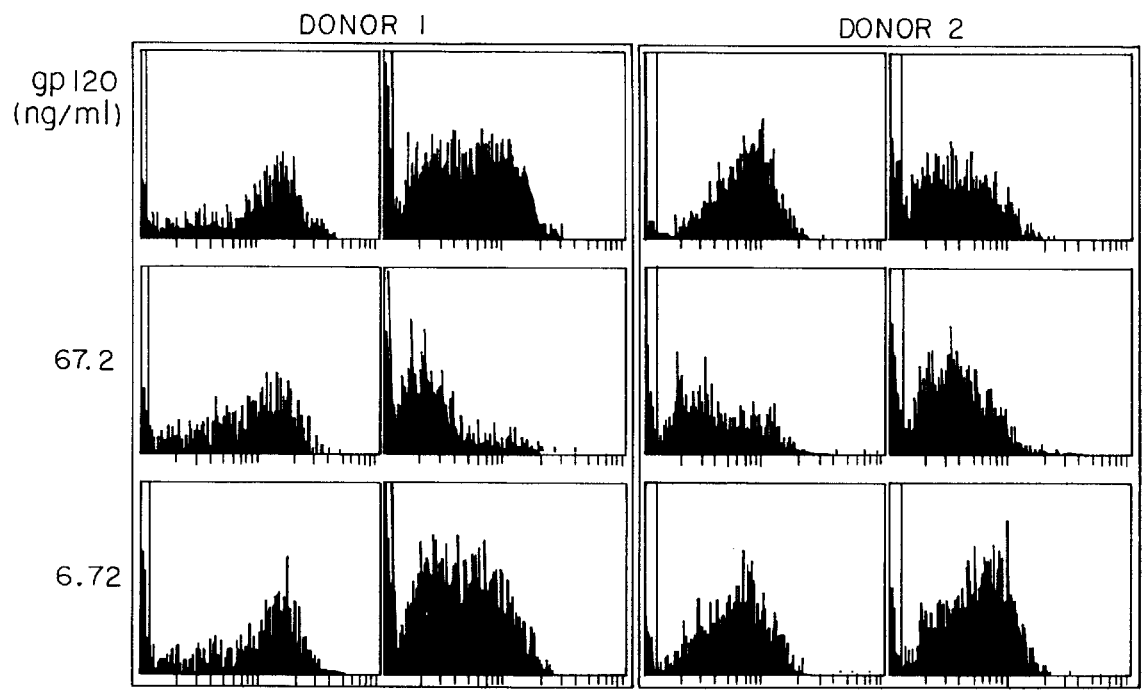
*Fig.6a* *Fig.6b*
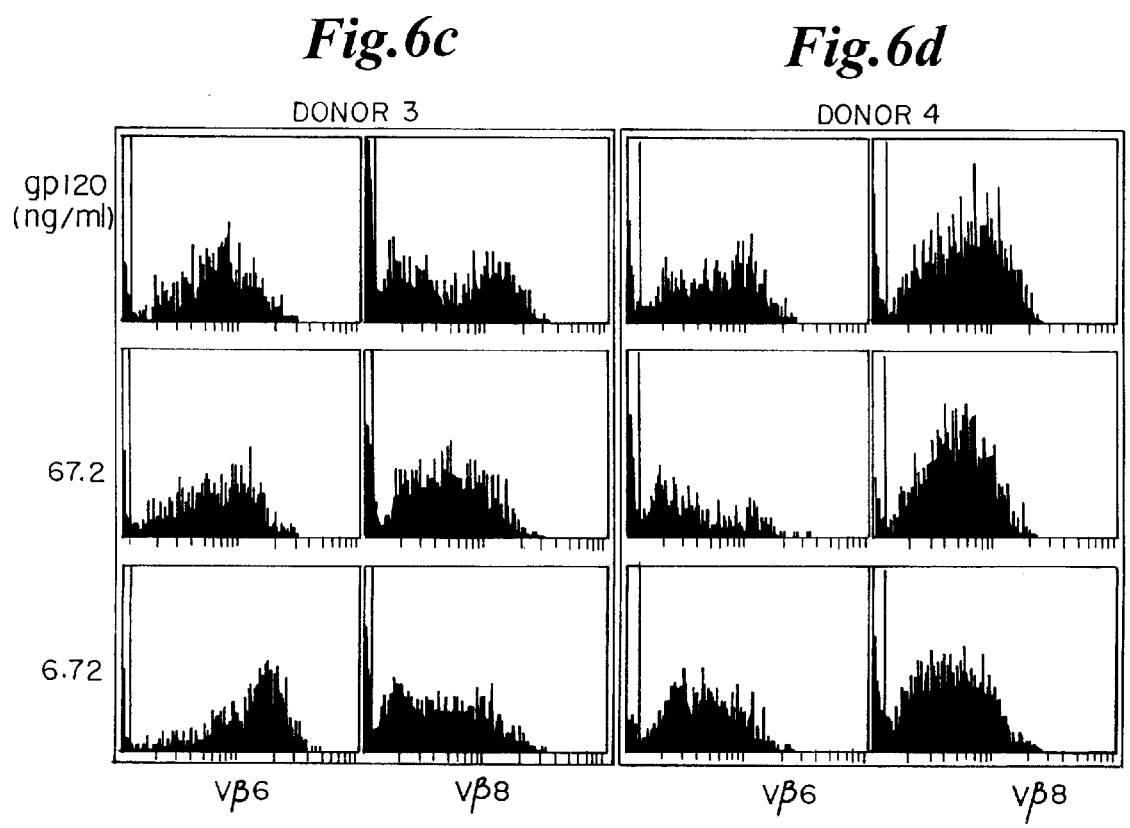
*Fig.6c* *Fig.6d*

DIAGNOSIS AND TREATMENT OF AIDS ONSET

This is a divisional of Ser. No. 07/973,485, filed Nov. 9, 1992 now abandoned.

BACKGROUND OF THE INVENTION

1. Field of the Invention

The present invention involves a method of assay of CD4+ T cells of a person infected with HIV to determine the immunodeficiency of the person. More specifically, the invention relates to a method of assay for the extent of depletion of subpopulations of CD4+ T cells which express specific β chains of the T cell receptor. The invention also involves additional assays, products, and methods of vaccination related to the above.

2. Description of Background Art

The importance of T cell counts in HIV infected individuals has already been recognized. Currently, the National Institute of Allergies and Infectious Diseases (NIAID) has recommended that the CD4+ T cell counts in HIV-infected patients be determined two to four times per year. Healthy individuals normally have 800–1000 CD4+ cells/µl of blood. NIAID recommends that AZT treatment begin when CD4 levels drops to 500 CD4+ cells/µl and that when levels drop below 200 CD4+ cells/µl that AZT be discontinued and pentamidine therapy be undertaken. CD4+ cell counts are currently performed using flow cytometry. FDA approval has recently been sought for a method of counting CD4+ cells by solubilizing CD4 receptors and quantifying by means of a microtiter calorimetric immunoassay.

The cause of T cell depletion in HIV infected individuals has remained a mystery, however. It is unlikely that T cell depletion is a direct result of HIV infection. Although HIV is known to infect CD4+ T cells by binding to the surface protein, only a fraction of CD4+ T cells, around 1 in 10000 are actually infected with the virus. A number of theories have been proposed to explain the depletion phenomenon but none have been proven or disproved.

One theory is that HIV requires the presence of another pathogen to deplete immune cell populations. The second pathogen may be opportunistic and depress the immune system simply by its presence. The second pathogen may also work as a "co-factor" working in concert with the HIV virus to directly suppress T cell populations. Mycoplasmas have been proposed as one candidate for co-factor pathogen status.

A second theory is that HIV triggers an autoimmune reaction that destroys immune cells. There is no agreement as to which of the possible markers on immune cells provides the binding site for the autoimmune antibodies. One group has proposed that antibodies to HIV envelope protein (gp120) could recognize and bind to the major histocompatibility (MHC) proteins. These anti-MHC antibodies would then cause the depletion of the T cells.

A third theory is that HIV-infected T cells fuse with uninfected cells to produce syncytia consisting of non-functioning cells. Thus, a single HIV-infected cell could bring about the demise of many non-infected T cells. The observation of syncytia formation was made in vitro, and no in vivo results have yet been published to substantiate this hypothesis.

Finally, some researchers have proposed that T cell depletion is caused by a HIV protein acting as a superantigen. Normally, when antigen is presented to a T cell, interaction of the alpha and beta chains of the T cell receptor with antigen is required for T cell activation. Superantigens interact only with the beta chain and are able to bypass the requirement of alpha chain interaction. By removing the alpha chain requirement, superantigens are able to activate a much larger proportion of the T cell subpopulation. Furthermore, T cells stimulated by superantigens eventually lose their ability to respond to antigens and undergo a programmed cell death known as apoptosis.

There is no agreement as to which HIV protein might have superantigen properties and, indeed, there has been no direct proof of superantigen involvement in T cell depletion. Some researchers have proposed that HIV gp120 may be the superantigen. Others have proposed that the nef gene produced by an open reading frame at the 3' end of the HIV genome may be the superantigen.

It is an object of the invention to delineate the pattern of T cell depletion in HIV infected individuals in order to develop effective intervention therapies to slow or halt T cell depletion and to more effectively time preventive treatment for opportunistic diseases.

SUMMARY OF THE INVENTION

The invention relates to a method of assay of CD4+ T cells of a person infected with HIV, preferably HIV-1, to determine the immunodeficiency of the person. This method involves measuring the extent of depletion of a CD4+ T cell subtype. The subtype is defined by the expression of a particular beta chain of the T cell receptor, having a constant region and a variable region (the variable region hereinafter designated TCR-Vβ or Vβ). The selection of the TCR-Vβs may be any of the TCR-Vβs, including TCR-Vβ14, TCR-Vβ15, TCR-Vβ16, TCR-Vβ17, TCR-Vβ18, TCR-Vβ19, or TCR-Vβ20.

In one embodiment of the foregoing assay a sample from the HIV infected person is isolated. The sample is prepared for contact with a binding agent specific to an analog of TCR-Vβ. The analog may be TCR-Vβ, a fragment of TCR-Vβ, mRNA encoding TCR-Vβ, mRNA encoding a fragment of TCR-Vβ, genomic DNA encoding TCR-Vβ, genomic DNA encoding a fragment of TCR-Vβ, cDNA encoding TCR-Vβ, or cDNA encoding a fragment of TCR-Vβ. The prepared sample is contacted with the binding agent under conditions suitable for binding of the binding agent and the analog. The extent of the binding is determined and a correlation is made to the extent of the depletion.

The binding agent in the foregoing assay may be an antibody, a fragment of an antibody, a binding receptor or a binding receptor fragment. The binding agent may also be a nucleic acid probe where the analog is in the form of mRNA, genomic DNA or cDNA.

Another embodiment of the foregoing assay involves isolating a sample from the HIV infected person. The sample is then prepared for contact with a first primer and a second primer. The first primer is substantially homologous to genomic DNA, mRNA or cDNA encoding a portion of the constant region of the TCR-β chain and the second primer is substantially homologous to genomic DNA, mRNA or cDNA encoding a portion of the variable region of the TCR-β chain. The prepared sample is contacted with the first and second primers and amplification enzymes under conditions suitable for amplification of the analog. The extent of the amplification is determined and a correlation is made to the extent of the depletion.

The first primer may be GTGCACCTCCTTCCCATT (SEQ ID NO: 1) and the second primer may be any one of the following:

(a) GCACAACAGTTCCCTGACTTGCAC (SEQ ID NO: 2);

(b) TCATCAACCATGCAAGCCTGACCT (SEQ ID NO: 3);

(c) GTCTCTAGAGAGAAGAAGGAGCGC (SEQ ID NO: 4);

(d) ACATATGAGAGTGGATTTGTCATT (SEQ ID NO: 5);

(e) ATACTTCAGTGAGACACAGAGAAAC (SEQ ID NO: 6);

(f) TTCCCTAACTATAGCTCTGAGCTG (SEQ ID NO: 7);

(g) AGGCCTGAGGGATCCGTCTC (SEQ ID NO: 8);

(h) CCTGAATGCCCCAACAGCTCTC (SEQ ID NO: 9);

(i) ATTTACTTTAACAACAACGTTCCG (SEQ ID NO: 10);

(j) CCTAAATCTCCAGACAAAGCTCAC (SEQ ID NO: 11);

(k) CTCCAAAAACTCATCCTGTACCTT (SEQ ID NO: 12);

(l) TCAACAGTCTCCAGAATAAGGACG (SEQ ID NO: 13);

(m) AAAGGAGAAGTCTCAGAT (SEQ ID NO: 14);

(n) CAAGGAGAAGTCCCCAAT (SEQ ID NO: 15);

(o) GGTGAGGGTACAACTGCC (SEQ ID NO: 16);

(p) GTCTCTCGAAAAGAGAAGAGGAAT (SEQ ID NO: 17);

(q) AGTGTCTCTCGACAGGCACAGGCT (SEQ ID NO: 18);

(r) AAAGAGTCTAAACAGGATGAGTCC (SEQ ID NO: 19);

(s) CAGATAGTAAATGACTTTCAG (SEQ ID NO: 20);

(t) GATGAGTCAGGAATGCCAAAGGAA (SEQ ID NO: 21);

(u) CAATGCCCCAAGAACTCACCCTGC (SEQ ID NO: 22);

(v) AGCTCTGAGGTGCCCCAGAATCTC (SEQ ID NO: 23);

(w) TTCTGCAGAGAGGCTCAAAGGACT (SEQ ID NO: 24);

(x) CTCAGTTGAAAGGCCTGATGGATC (SEQ ID NO: 25);

(y) CTCAGCTCAACAGTTCAGTGACTA (SEQ ID NO: 26); and (z) CCAATCCAGGAGGCCGAACACTTC (SEQ ID NO: 27).

The invention further relates to a method of assay of an antibody-containing fluid of a person infected with HIV to determine the immunodeficiency of the person. The method involves isolating a sample from the HIV-infected person, where the sample is suspected to contain an antibody having a paratope specific to the variable region of a TCR-β chain (TCR-Vβ). The sample is prepared for contact with a binding agent specific to the paratope of the antibody. The prepared sample is contacted with the binding agent under conditions suitable for binding of the antibody with the binding agent. The extent of the binding is determined and a correlation is made to the extent of the depletion. In a preferred embodiment of the foregoing assay, the paratope of the antibody may be specific to an epitope on any one of the following: Ser-Ala-Val-Ile-Ser-Gln-Lys-Pro-Ser-Arg-Asp-Ile-Cys-Gln-Arg-Gly-Thr-Ser-Leu-Thr (SEQ ID NO: 28); Gln-Leu-Gln-Glu-Thr-Glu-Asn-His-Lys-Lys-Arg-Phe-Ser-Ser-Gln-Cys-Pro (SEQ ID NO: 29); Gln-Asn-Leu-Ser-Ala-Ser-Arg-Pro-Gln-Asp-Arg-Gln-Phe-Ile-Leu-Ser-Ser-Lys (SEQ ID NO: 30); Asp-Gly-Tyr-Ser-Val-Ser-Arg-Ser-Lys-Thr-Glu-Asp-Phe-Leu-Leu (SEQ ID NO: 31); Pro-Arg-Asn-Arg-Ile-Thr-Lys-Ile-Gly-Lys-Arg-Ile-Met-Leu-Glu-Cys (SEQ ID NO: 32); or Pro-Arg-His-Leu-Val-Arg-Arg-Arg-Gly-Gln-Glu-Ala-Arg-Leu-Arg-Cys (SEQ ID NO: 33). The paratope may alternatively be specific to an epitope on a TCR-Vβ which is one of the following: TCR-Vβ14, TCR-Vβ15, TCR-Vβ16, TCR-Vβ17, TCR-Vβ18, TCR-Vβ19, and TCR-Vβ20. The paratope of the antibody, in addition to the above specificities, may also be specific to an epitope on gp120 of HIV. In another embodiment of the foregoing assay, the binding agent may be an antibody, an antibody fragment, a binding receptor, or a polypeptide containing fewer than 100 amino acids.

The invention further relates to a binding agent specific to a paratope on a human antibody. The paratope on the antibody is specific to an epitope on a TCR-Vβ. The binding agent may be an antibody or an antibody fragment. The antibody may be a binding receptor or a binding receptor fragment. The binding agent may also be described as a polypeptide containing fewer than 100 amino acids. In a preferred embodiment, the epitope on the binding agent may be on an amino acid sequence which is one of the following: Ser-Ala-Val-Ile-Ser-Gln-Lys-Pro-Ser-Arg-Asp-Ile-Cys-Gln-Arg-Gly-Thr-Ser-Leu-Thr (SEQ ID NO: 28); Gln-Leu-Gln-Glu-Thr-Glu-Asn-His-Lys-Lys-Arg-Phe-Ser-Ser-Gln-Cys-Pro; Gln-Asn-Leu-Ser-Ala-Ser-Arg-Pro-Gln-Asp-Arg-Gln-Phe-Ile-Leu-Ser-Ser-Lys; Asp-Gly-Tyr-Ser-Val-Ser-Arg-Ser-Lys-Thr-Glu-Asp-Phe-Leu-Leu; Pro-Arg-Asn-Arg-Ile-Thr-Lys-Ile-Gly-Lys-Arg-Ile-Met-Leu-Glu-Cys; or Pro-Arg-His-Leu-Val-Arg-Arg-Arg-Gly-Gln-Glu-Ala-Arg-Leu-Arg-Cys.

The invention further relates to a method of assay of the fluids of a person infected with HIV to determine the immunodeficiency of the person. The method involves isolating a sample from the HIV infected person, where the sample is suspected to contain an antibody having a paratope specific to an epitope on a TCR-Vβ and being bound to the TCR-Vβ by the paratope to form an antibody-TCR-Vβ pair. The sample is prepared for contact with a binding agent which selectively binds to the antibody-TCR-Vβ pair. The binding agent does not bind to the antibody when the antibody is not bound to TCR-Vβ and the binding agent does not bind to the TCR-Vβ when the antibody is not bound to TCR-Vβ. The prepared sample is contacted with the binding agent under conditions suitable for binding of the binding agent to any TCR-Vβ-pair. The extent of the binding is determined and a correlation is made to the presence or amount of such antibody-TCR-Vβ pairing.

The invention further relates to a method of treatment of a person infected with HIV to attenuate or avert immunodeficiency in the person infected with HIV. The method involves inoculating the person infected with HIV with a binding agent which is substantially homologous with an epitope on a TCR-Vβ and which is reactive with a paratope on a free antibody in the person's blood, where the paratope is specific to the epitope on the TCR-Vβ. The binding agent may be a polypeptide, a binding receptor or a binding receptor fragment. The binding agent may also be an antiidiotypic antibody or an antiidiotypic antibody fragment. An antiidiotypic antibody is specific to the paratope of another antibody (ie. binding of the antiidiotypic antibody prevents the other antibody from being able to bind to an epitope).

Antiidiotypic antibody fragments useful in the invention are those fragments of antiidiotypic antibodies which possess the ability to prevent an antibody from being able to bind to an epitope.

The invention further relates to another method of treatment of a person infected with HIV to attenuate or avert immunodeficiency. The method involves removing blood from the person infected with HIV; removing antibody from the blood of the person, the antibody having a paratope specific to an epitope present on TCR-Vβ and reintroducing the blood into the person.

The invention finally relates to a method of vaccination of a person infected with HIV or a person at risk for infection with HIV in order to attenuate or avert immunodeficiency. The method involves inoculating the person with an immunogenic substance capable of raising antiidiotypic antibodies in the person. The antiidiotypic antibodies are specific to free antibodies containing a paratope specific to an epitope on a TCR-Vβ.

BRIEF DESCRIPTION OF THE DRAWINGS

FIG. 6 shows the results of cytofluorimetric analysis of cell surface Vβ6 and Vβ8 modulation in four healthy donors, after the stimulation of lymphocytes with a mixture of Staphylococcal enterotoxins B, C2 and E, and an overnight incubation with HIV gp120.

DETAILED DESCRIPTION OF THE INVENTION

Figure 1:
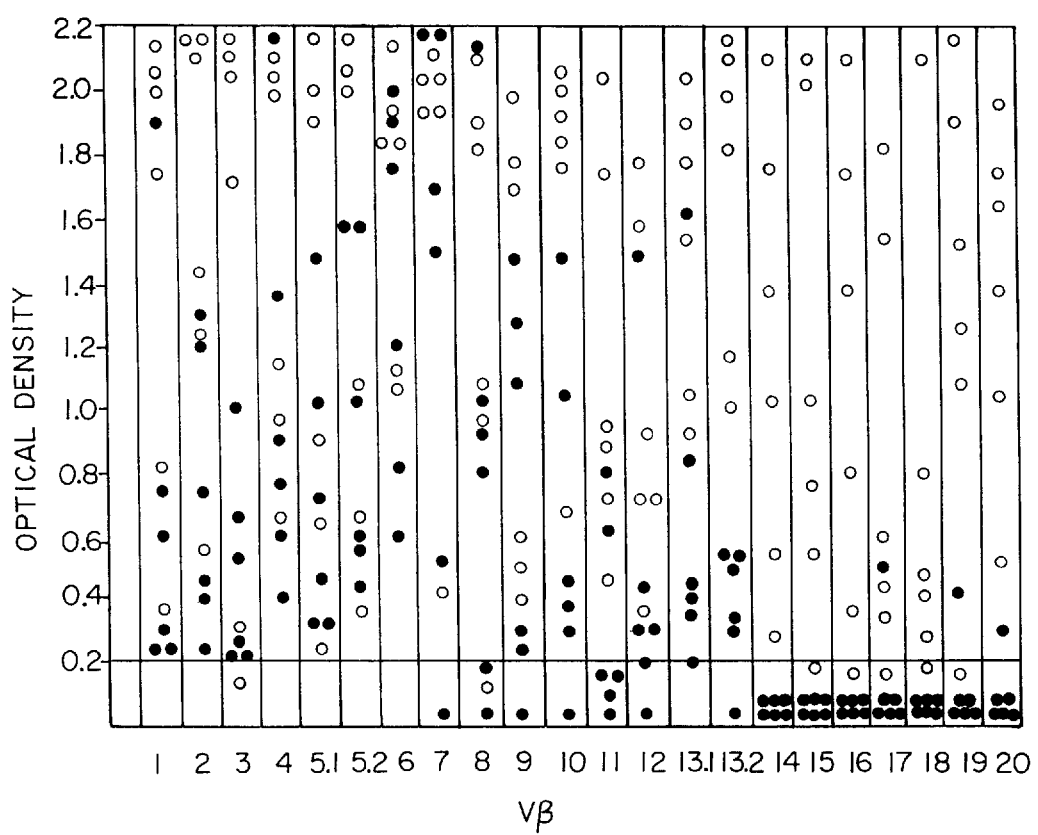
FIG. 1 shows the expression of the T cell receptor Vβ genes in T cells from HIV infected individuals and from healthy controls.

The invention relates to a method of assay of CD4+ T cells of a person infected with a Human Immunodeficiency Virus (HIV) to determine the immunodeficiency of the person. In a preferred embodiment, HIV is HIV-1. HIV-1 is also known as HTLV-III or LAV. This method involves measuring the extent of depletion of a CD4+ T cell subtype as defined by the expression of a particular TCR-Vβ on the surface of the T cell as a component of the T cell receptor. The selection of the TCR-Vβs may include any TCR-Vβ subtype. A TCR-Vβ subtype is defined as any single member of a TCR-Vβ subfamily (eg. TCR-Vβ1, TCR-Vβ5.1, TCR-Vβ5.2, etc.). It is preferred to include the TCR-Vβ14, TCR-Vβ15, TCR-Vβ16, TCR-Vβ17, TCR-Vβ18, TCR-Vβ19, or TCR-Vβ20 subtypes in the assay.

In one embodiment of the foregoing assay a sample from the HIV infected person is isolated. The sample is prepared for contact with a binding agent specific to a TCR-Vβ subtype which may be the TCR-Vβ protein, a fragment of the TCR-Vβ protein, mRNA encoding the TCR-Vβ, mRNA encoding a fragment of the TCR-Vβ, genomic DNA encoding TCR-Vβ, genomic DNA encoding a fragment of TCR-Vβ, cDNA encoding TCR-Vβ, or cDNA encoding a fragment of TCR-Vβ. The sample is preferably blood, although any fluid containing a representative population of CD4+ T cells will work with the method. The prepared sample is contacted with the binding agent under conditions suitable for binding of the binding agent and the analog. The extent of the binding is determined and a correlation is made to the extent of the depletion.

Where the analog is the TCR-Vβ protein or a fragment of the TCR-Vβ protein the binding agent in the foregoing assay may be an antibody, a fragment of an antibody, a binding receptor, or a binding receptor fragment which selectively recognize and bind to portions of the TCR-Vβ protein. If a fragment of an antibody is used as the binding agent, the only requirement of the fragment is that the fragment is able to specifically recognize and bind to any one TCR-Vβ subtype. A receptor may be any non-immunoglobulin protein which is ordinarily found on the surface of any cell type. The receptor may be prepared by any conventional means which involves freeing the receptor from the cell membrane and isolating the receptor in a substantially pure form. Alternatively, the receptor may be prepared by recombinant DNA methods, including producing the receptor in a transformed host and isolating the receptor in a substantially pure form. The analog may be the TCR-Vβ protein which is present on intact T cells. In this case, flow cytometry may be used to determine the extent to the binding of the analog. The analog may also be the TCR-Vβ protein or a fragment of the TCR-Vβ protein which has been released from T cells by solubilization of the membranes, by peptidase treatment of the cells or other methods known in the art. The extent of binding in this case may be determined by immunoassays known in the art, including sandwich immunoassays, competitive immunoassays or other assay formats known in the art.

The binding agent may also be a nucleic acid probe where the analog is in the form of mRNA, genomic DNA or cDNA. The sequence of the probe is substantially homologous to the sequence of any one TCR-Vβ subtype and will preferentially hybridize to any nucleic acid encoding the same type of specific TCR-Vβ under appropriate hybridization conditions. Methods of predicting appropriate hybridization conditions or determining such conditions are known in the art. The probe may be labelled by any conventional method, including labelling with $^{32}$P- or $^{35}$S- tagged nucleotides at one end or throughout the probe, labelling with biotin-tagged nucleotides, and chemiluminescent labelling. Alternatively, a second probe may be utilized in a sandwich or other format to detect the binding of this above probe.

Where the analog is mRNA or cDNA which is prepared from the total RNA or mRNA present in a sample, there is no need to isolate subpopulations of cells from the sample. However, it is preferable to isolate peripheral blood mononuclear cells and isolate total RNA from these cells prior to preparing cDNA. Where the analog is genomic DNA, any cell which does not express a specific TCR-Vβ may be removed from the sample so that the genomic DNA is indicative of the presence of the specific TCR-Vβ subtype.

Another embodiment of the foregoing assay involves isolating a sample from the HIV infected person and preparing the sample for contact with a first primer and a second primer. A preferred method of preparation is performed by isolation of peripheral blood mononuclear cells, isolation of total RNA from the cells and first strand synthesis of cDNA. The primers are oligonucleotides which can be prepared on commercially available synthesis machines or ordered from a company providing such services. The oligonucleotides are preferably DNA, although any nucleic acid may be used provided that the primer is able to hybridize to the nucleic acid analog and is also able to function in amplification reactions.

The first primer is substantially homologous to genomic DNA, mRNA or cDNA encoding a portion of the constant region of the TCR-β chain and the second primer is substantially homologous to genomic DNA, mRNA or cDNA encoding a portion of the variable region of the TCR-β chain. The second primer must be capable of selectively binding to a sequence within any TCR-Vβ coding sequence in order to insure that only nucleic acids encoding TCR-Vβ of the desired subtype are amplified in the following steps. The prepared sample is contacted with the first and second primers and amplification enzymes under conditions suitable for amplification of the analog. In a preferred embodiment, amplification is performed using the polymerase chain reaction (PCR) utilizing Vβ- and Cβ-specific primers shown in Table II. Other amplification techniques which use the analog as a template and are capable of reproducing a portion of the analog or its corresponding opposite strand, such as the ligase chain reaction, may also be employed. The extent of the amplification is determined and a correlation is made to the extent of the depletion. The extent of amplification may also be determined using a DNA Enzyme Immunoassay (DEIA) kit available from Sorin Biomedica S.p.A. (Saluggia (VC), Italy)

The invention further relates to a method of assay of an antibody-containing fluid of a person infected with HIV to determine the immunodeficiency of the person, where the sample is suspected to contain an antibody having a paratope specific to a TCR-Vβ subtype. A paratope is defined as that portion of an antibody which enables the antibody to recognize and selectively bind to an epitope. The sample is prepared for contact with a binding agent specific to the paratope of the antibody. The prepared sample is contacted with the binding agent under conditions suitable for binding of the antibody with the binding agent. The extent of the binding is determined and a correlation is made to the extent of the depletion. The extent of the binding can be determined by conventional methods, as indicated above.

In another embodiment of the foregoing assay, the paratope of the antibody may be specific to an epitope which is present on a peptide and the peptide is one of the following: Ser-Ala-Val-Ile-Ser-Gln-Lys-Pro-Ser-Arg-Asp-Ile-Cys-Gln-Arg-Gly-Thr-Ser-Leu-Thr; Gln-Leu-Gln-Glu-Thr-Glu-Asn-His-Lys-Lys-Arg-Phe-Ser-Ser-Gln-Cys-Pro; Gln-Asn-Leu-Ser-Ala-Ser-Arg-Pro-Gln-Asp-Arg-Gln-Phe-Ile-Leu-Ser-Ser-Lys; Asp-Gly-Tyr-Ser-Val-Ser-Arg-Ser-Lys-Thr-Glu-Asp-Phe-Leu-Leu; Pro-Arg-Asn-Arg-Ile-Thr-Lys-Ile-Gly-Lys-Arg-Ile-Met-Leu-Glu-Cys; or Pro-Arg-His-Leu-Val-Arg-Arg-Arg-Gly-Gln-Glu-Ala-Arg-Leu-Arg-Cys. Peptides may be prepared by solid phase peptide synthesis techniques, recombinant DNA techniques or otherwise.

The paratope may also be specific to an epitope on a TCR-Vβ with, which is one of the following: TCR-Vβ14, TCR-Vβ15, TCR-Vβ16, TCR-Vβ17, TCR-Vβ18, TCR-Vβ19, and TCR-Vβ20. The paratope of the antibody may also be specific to an epitope on gp120 of HIV.

In another embodiment of the foregoing assay, the binding agent may be an antibody, an antibody fragment, a binding receptor, a binding receptor fragment, or a polypeptide containing fewer than 100 amino acids where the polypeptide is capable of recognizing and selectively binding to the paratope.

The invention further relates to a binding agent specific to a paratope on a human antibody. The paratope on the antibody is specific to an epitope on a TCR-Vβ. The binding agent may itself be an antibody or an antibody fragment. The binding agent may be a binding receptor or a binding receptor fragment. The binding agent may also be described as a polypeptide containing fewer than 100 amino acids. The epitope on the binding agent may be on an amino acid sequence which is one of the following: Ser-Ala-Val-Ile-Ser-Gln-Lys-Pro-Ser-Arg-Asp-Ile-Cys-Gln-Arg-Gly-Thr-Ser-Leu-Thr; Gln-Leu-Gln-Glu-Thr-Glu-Asn-His-Lys-Lys-Arg-Phe-Ser-Ser-Gln-Cys-Pro; Gln-Asn-Leu-Ser-Ala-Ser-Arg-Pro-Gln-Asp-Arg-Gln-Phe-Ile-Leu-Ser-Ser-Lys; Asp-Gly-Tyr-Ser-Val-Ser-Arg-Ser-Lys-Thr-Glu-Asp-Phe-Leu-Leu; Pro-Arg-Asn-Arg-Ile-Thr-Lys-Ile-Gly-Lys-Arg-Ile-Met-Leu-Glu-Cys; or Pro-Arg-His-Leu-Val-Arg-Arg-Arg-Gly-Gln-Glu-Ala-Arg-Leu-Arg-Cys.

The invention further relates to another method of assay of the fluids of a person infected with HIV to determine the immunodeficiency of the person. The method involves isolating a sample of a fluid from the HIV infected person where the sample is suspected to contain an antibody having a paratope specific to an epitope on a TCR-Vβ and being bound to the TCR-Vβ by the paratope to form an antibody-TCR-Vβ pair. The sample is preferably blood or a blood fraction, although any bodily fluid which may contain an antibody-TCR-Vβ pair may be used. The sample is prepared for contact with a binding agent which selectively binds to the antibody-TCR-Vβ pair. The binding agent does not bind to the antibody when the antibody is not bound to TCR-Vβ (ie. when the antibody is not a component of an antibody-TCR-Vβ pair) and the binding agent does not bind to the TCR-Vβ when the antibody is not bound to TCR-Vβ (ie. when the antibody is not a component of an antibody-TCR-Vβ pair). The prepared sample is contacted with the binding agent under conditions suitable for binding of the binding agent to any TCR-Vβ-pair. The extent of the binding is determined and a correlation is made to the extent of the depletion. The extent of binding is determined by conventional methods as described above.

In many of the foregoing assays a sample is prepared for binding with a binding agent. In the case where blood is used, it may be helpful to convert the blood to serum. In some cases further processing of the serum (eg. by centrifugation to isolate certain cell types) may be necessary. Steps to correlate the extent of binding to the extent of depletion may be accomplished by running standards containing known amount of analog, antibody or antibody-TCR-Vβ-pair in the assays and developing a standard curve for use with experimental samples.

The invention further involves a method of treatment of a person infected with HIV to attenuate or avert immunodeficiency in the person infected with HIV. The method involves inoculating the person infected with HIV with a binding agent which is substantially homologous with an epitope on TCR-Vβ and which is reactive with a paratope in a free antibody in the person's blood, where the paratope is specific to the epitope on the TCR-Vβ. Inoculation includes introduction of the immunogen (ie. the binding agent) by ingestion (eg. orally) or by injection by any conventional means (eg. intramuscular injection or transfusion). The binding agent may be a polypeptide, a binding receptor or a binding receptor fragment as above. The binding agent may also be an antiidiotypic antibody or an antiidiotypic antibody fragment where the fragment possesses the ability to bind to a paratope in a free antibody in the person's blood.

The invention further relates to another method of treatment of a person infected with HIV to attenuate or avert immunodeficiency. The method involves removing blood from the person infected with HIV, removing antibody from the blood of the person, the antibody having a paratope specific to an epitope present on TCR-Vβ and reintroducing the blood into the person. The antibody can be removed by conventional means such as pheresis.

The invention finally relates to a method of vaccination of a person infected with HIV or a person at risk for infection with HIV in order to attenuate or avert immunodeficiency. The method involves inoculating the person with an immunogenic substance capable of raising antiidiotypic antibodies in the person. Inoculation includes introduction of the immunogen by ingestion (eg. orally) or by injection by any conventional means (eg. intramuscular injection). The antiidiotypic antibodies are specific to free antibodies containing a paratope specific to an epitope on a TCR-Vβ.

Aspects of the invention may be illustrated by the following examples.

EXAMPLES

Example 1

Lymphocyte Preparation from HIV+ Patients and Controls

Ten ml of blood was drawn from six healthy volunteers (blood donors), from six symptomatic HIV+ patients with a history of major opportunistic infection and CD4 lymphocyte counts of less that 200/mm³ (group 1, CDC stage IVC), from asymptomatic HIV+ patients with severe lymphocytes depletion (CD4+ lymphocyte count <200/mm³), but without malignancy or opportunistic infection (group 2, stage CDC III), and from asymptomatic patients who were HIV+ for more than 5 years and had normal lymphocyte numbers (group 3, stage CDC II). Table I shows the clinical parameters of these patients.

TABLE I

Clinical Parameters of 14 HIV Seropositive Patients

| Group | Patients | Age | Sex | CD n/mmc | Staging CDC |
|---|---|---|---|---|---|
| 1 | A | 22 | F | 25 | IVC1 |
|   | B | 36 | M | 1 | IVC1 |
|   | C | 28 | M | 17 | IVC1 |
|   | D | 41 | M | 21 | IVC1 |
|   | E | 46 | M | 13 | IVC1 |
|   | F | 31 | M | 10 | IVC1 |
| 2 | G | 30 | M | 100 | III |

TABLE I-continued

Clinical Parameters of 14 HIV Seropositive Patients

| Group | Patients | Age | Sex | CD n/mmc | Staging CDC |
|---|---|---|---|---|---|
|   | H | 30 | M | 196 | III |
|   | I | 26 | M | 147 | III |
|   | J | 30 | M | 156 | III |
| 3 | K | 37 | M | 851 | II |
|   | L | 25 | F | 852 | II |
|   | M | 27 | M | 827 | II |
|   | N | 38 | M | 825 | II |

1 = AIDS patients
2 = Patients with severe immune depletion (CD4 < 200/mmc), but witnout AIDS
3 = Patients with long history of HIV infection (>5 years) without a severe depletion of CD4 lymphocytes Peripheral blood mononuclear cells (PBMCs) were prepared from the above patient samples by Fycoll Hypaque gradient centrifugation at 2000 rpm, corresponding to 1645 g (Centrifuge Haereus, Omnifuge 2.0 RS, rotor 2250).

Total RNA was prepared from about $0.5 \times 10^7$ to $1 \times 10^7$ PBMCs by the guanidine isothiocyanate-phenol-chloroform extraction method. PBMCs were washed 3 times with Phosphate Buffered Saline (PBS) and resuspended in 1 ml of a solution containing 4M guanidine isothiocyanate; 25 mM sodium citrate, pH 7.0; 0.5% sarcosyl; and 0.1M β-mercaptoethanol. 0.1 ml of 2M sodium acetate, pH 4.0; 1 ml of phenol and 0.2 ml of chloroform-isoamyl alcohol mixture (1:49) were sequentially added to lysed cells and the resulting preparation was vigorously shaken, cooled on ice for 15 min and centrifuged at 10,000 g for 20 min at 4° C. The RNA, present in the aqueous phase, was mixed with 1 ml of isopropanol and left for 1 h at −20° C. The RNA pellet, resulted from a further centrifugation, was dissolved in guanidine isothiocyanate solution and precipitated with isopropanol at −20° C. for 1 h. The RNA pellet was resuspended in 75% ethanol, vacuum dried and dissolved in 50 μl of $H_2O$, 0.1% diethylpyrocarbonate.

Two μg of the RNA preparation was used to synthesize the first strand of the complementary DNA (cDNA) with a Riboclone cDNA Synthesis System, Promega Corp. (Madison, Wis.), using the instructions from the manufacturer.

For the analysis of the expression of human T cell receptor (TCR) Vα and Vβ repertoire, 19 Vα, 22 Vβ, 2 Cα and 2 Cβ specific oligonucleotides, one of which was chosen to match a common sequence near to the 5' ends of the Cβ1 and Cβ2 genes, were prepared. The sequences of the oligonucleotides, reported in Table II, were obtained from previously published reports and were selected to contain roughly the same G+C content as the other primers.

TABLE II

T Cell Receptor α-Chain Primers (5' → 3'):

| $V_α1$, | CTGAGGTGCAACTACTCA (SEQ ID NO:36) |
|---|---|
| $V_α2$, | AGAGGGAGCCTTAGCCTCTCTCAA (SEQ ID NO:37) |
| $V_α3$, | AATGCCACCATGAACTGCAGTTAC (SEQ ID NO:38) |
| $V_α4$, | ACAAGCATTACTGTACTCCTA (SEQ ID NO:39) |
| $V_α5$, | GGCCCTGAACATTCAGGA (SEG ID NO:40) |
| $V_α6$, | TGACCAGCAAAATGCAACAGAAGG (SEQ ID NO:41) |
| $V_α7$, | AGGAGCCATTGTCCAGATAAA (SEQ ID NO:42) |
| $V_α8$, | GCTTATTCAAACAGCGCCTCAGAC (SEQ ID NO:43) |
| $V_α9$, | CAGAGAGTGACTCAGCCCGAGAAG (SEQ ID NO:44) |
| $V_α10$, | ACCCAGCTGGTGGAGCAGAGCCCT (SEQ ID NO:45) |

TABLE II-continued

T Cell Receptor α-Chain Primers (5' → 3'):

| | |
|---|---|
| V$_α$11, | AGAAAGCAAGGACCAAGTGTT (SEQ ID NO:46) |
| V$_α$12, | CACAACCTAACTCAAGCGCAGACT (SEQ ID NO:47) |
| V$_α$13, | CTCATCAACCTGTTTTACATTCCC (SEQ ID NO:48) |
| V$_α$14, | GCAGCTTCCCTTCCAGCAAT (SEQ ID NO:49) |
| V$_α$15, | AGAACCTGACTGCCCAGGAA (SEQ ID NO:50) |
| V$_α$16, | CCTCCAGTTCCTTCTGAA (SEQ ID NO:51) |
| V$_α$17, | CAGCAGGTGAAACAAAGTCCTCAA (SEQ ID NO:52) |
| V$_α$18, | TGTCAGGCAATGACAAGG (SEQ ID NO:53) |
| V$_α$22, | TACACAGCCACAGGATACCCTTCC (SEQ ID NO:54) |
| C$_α$3', | ATGTCTAGCACAGTTTTGTCTGTG (SEQ ID NO:55) |
| C$_α$5', | ATATCCAGAACCCTGACCCTGCCG (SEQ ID NO:56) |
| C$_α$NH$_2$ | CAGTGACAAGTGTGTCTGCCTATTCACCGA (SEQ ID NO:57) |
| V$_β$1, | GCACAACAGTTCCCTGACTTGCAC (SEQ ID NO:2) |
| V$_β$2, | TCATCAACCATGCAAGCCTGACCT (SEQ ID NO:3) |
| V$_β$3, | GTCTCTAGAGAGAAGAAGGAGCGC (SEQ ID NO:4) |
| V$_β$4, | ACATATGAGAGTGGATTTGTCATT (SEQ ID NO:5) |
| V$_β$5.1, | ATACTTCAGTGAGACACAGAGAAAC (SEQ ID NO:6) |
| V$_β$5.2, | TTCCCTAACTATAGCTCTGAGCTG (SEQ ID NO:7) |
| V$_β$6, | AGGCCTGAGGGATCCGTCTC (SEQ ID NO:8) |
| V$_β$7, | CCTGAATGCCCCAACAGCTCTC (SEQ ID NO:9) |
| V$_β$8, | ATTTACTTTAACAACAACGTTCCG (SEQ ID NO:10) |
| V$_β$9, | CCTAAATCTCCAGACAAAGCTCAC (SEQ ID NO:11) |
| V$_β$10, | CTCCAAAAACTCATCCTGTACCTT (SEQ ID NO:12) |
| V$_β$11, | TCAACAGTCTCCAGAATAAGGACG (SEQ ID NO:13) |
| V$_β$12, | AAAGGAGAAGTCTCAGAT (SEQ ID NO:14) |
| V$_β$13.1, | CAAGGAGAAGTCCCCAAT (SEQ ID NO:15) |
| V$_β$13.2, | GGTGAGGGTACAACTGCC (SEQ ID NO:16) |
| V$_β$14, | GTCTCTCGAAAAGAGAAGAGGAAT (SEQ ID NO:17) |
| V$_β$15, | AGTGTCTCTCGACAGGCACAGGCT (SEQ ID NO:18) |
| V$_β$16, | AAAGAGTCTAAACAGGATGAGTCC (SEQ ID NO:19) |
| V$_β$17, | CAGATAGTAAATGACTTTCAG (SEQ ID NO:20) |
| V$_β$18, | GATGAGTCAGGAATGCCAAAGGAA (SEQ ID NO:21) |
| V$_β$19, | CAATGCCCCAAGAACTCACCCTGC (SEQ ID NO:22) |
| V$_β$20, | AGCTCTGAGGTGCCCCAGAATCTC (SEQ ID NO:23) |
| V$_β$21, | TTCTGCAGAGAGGCTCAAAGGACT (SEQ ID NO:24) |
| V$_β$22, | CTCAGTTGAAAGGCCTGATGGATC (SEQ ID NO:25) |
| V$_β$23, | CTCAGCTCAACAGTTCAGTGACTA (SEQ ID NO:26) |
| V$_β$24, | CCAATCCAGGAGGCCGAACACTTC (SEQ ID NO:27) |
| C$_β$3', | GTGCACCTCCTTCCCATT (SEQ ID NO:1) |
| C$_β$5', | GTCCTGTGTTTGAGCCATCAGAA (SEQ ID NO:34) |
| C$_β$NH$_2$ | ACCCAAAAGGCCACACTGGTGTGCCTGGCC (SEQ ID NO:35) |

All the primers were prepared using a DNA synthesizer (PCR Mate 391-EP; Applied Biosystem, Foster City, Calif.). Aliquots of cDNA (1μl, corresponding to 1/25 of the initial amount of RNA) were analyzed separately by amplification using TCR Vβ and a Cβ region specific primers. One μl of each of the cDNAs was combined in 100 μl of reaction volume with an amplification mixture containing 4 U of DNA polymerase (Tth DNA Polymerase from *Thermus thermophilus* HB8; Toyobo, Osaka, Japan); dNTP, at the final concentration of 250 μM each; 50 pmoles of each primer, in a buffer prepared with 67 mM Tris.HCl, pH 8.8; 16.6 mM (NH$_4$)$_2$SO$_4$; 10 mM β-mercaptoethanol; 6.7 βM EDTA; 1.5 mM MgCl$_2$ and 170 μg/ml of BSA.

The final reaction volume was brought to 100 μl with double distilled H$_2$O and the mixture was overlaid with 50 μl of mineral oil, heated in water bath at 95° C. for 5 min and cooled rapidly on ice, in order to denature the DNA/RNA complexes. The reaction was taken through 40 cycles in a thermal automatic cycler (Perkin-Elmer Thermal Cycler; Norwalk, Conn.), with each cycle consisting of 94° C. for 1 min (denaturation step), 55° C. for 1 min (annealing step), 72° C. for 1.5 min (elongation step).

Example 4

DNA Enzyme Immunoassay (DEIA)

The assay for the presence or absence of each amplification product was carried out using an assay containing an antibody specific to double stranded DNA (available as DEIA assay by Sorin Biomedica S.p.A., Saluggia(VC), Italy). The expression of each V gene transcript was operationally defined by an optical density value obtained with the DEIA test, performed using a Cβ or a Cα specific capture probe, mapping to a region internal to the amplified cDNA. The test is based on a monoclonal antibody that recognizes double stranded, but not single stranded DNA. Thus, the antibody can only react with the solid phase if the amplified product is complementary to the immobilized probe. The sensitivity and the specificity of the DEIA assay is similar to conventional Southern blot.

The CαNH$_2$ and CβNH$_2$ oligonucleotides used as capture probes (for sequences, see Table II) were modified and biotinylated at the 5' end. The modification was achieved by introducing a primary amino group during the synthesis using Aminolink 2 (Applied Biosystems). Five nmol of modified oligonucleotides, resuspended in 10 μl of double distilled H$_2$O, were mixed with 17 μl of a solution of N-hydroxysuccinamidobiotin in N,N-dimethylformamide (145 mmol/l). After an overnight incubation, the biotinylated oligonucleotides were purified by filtration through a Sephadex G-15 column (Pharmacia, Uppsala, Sweden) according to the manufacturer's instructions.

According to the DEIA assay protocol, streptavidin coated 96 microliter plates were incubated overnight at 4° C. with 5 ng/well of biotinylated CαNH$_2$ or CβNH$_2$ oligonucleotides in 100 μl of TE (Tris 10 mM, pH 8.0; 1 mM EDTA, pH 8.0). The solid phase was washed 5 times with 200 μl of washing solution (6.7 mM phosphate buffer, pH 6.1; 0.13M sodium chloride; 0.004% Cialit and 0.1% Tween 20).

The amplification mixtures from Example 3 were denatured on a heat block for 10 min at 100° C. and then quickly cooled on ice. Twenty μl of the amplification product, diluted 5 times in hybridization solution (1× SSC, 2× Denhardt's solution, 10 mM Tris-HCl, pH 7.5, 1 mM EDTA), were added to the coated wells and incubated for 1 h at 50° C. After 5 washes with washing solution, each well received 100 μl of a 1/1000 dilution in PBS-10% Fetal Calf Serum (FCS) of a standard preparation of the 27 14-D9 mAb, specific to double stranded DNA.

After 2 h incubation at 37° C. and 5 washes with washing solution, the bound antibody was revealed with 100 μl of HRP-labeled rabbit anti-mouse IgG antibody (ICN Biochemical, High Wycombe, Bucks, England) diluted 1/20,000 in PBS10% FCS. Following 1 h incubation at room temperature and 5 washes, the wells received 100 μl of the chromogen/substrate solution (0.1M citrate buffer, pH 5, containing phenylenediamine hydrochloride and 10 μl of H$_2$O$_2$) and the calorimetric reaction was allowed to develop for 30 min at room temperature in the dark. After blocking with 200 μl of 1N sulfuric acid, the net absorbance was read in a spectrophotometer at 450 nm.

The expression of most of the known TCR Vα and Vβ genes was analyzed by amplification of mRNA from PBMCs obtained from 6 patients affected by AIDS and from 6 normal healthy individuals. Total RNA was separated from each sample immediately after collection and, at the time of analysis, was reverse transcribed in cDNA, as described in Example 1. Aliquots of cDNA were amplified, as described in Example 3, with each of the 22 5' Vβ-specific sense primers and a 3' Cα-specific antisense primer or with each of the 19 5' Vα specific sense primers and a 3' Cα-specific antisense primer. Altogether, these primers are expected to cover most of the sequenced human TCR Vα and Vβ genes.

Although the oligonucleotides specific to Vβ21-24 were not used in the current example, one could also use these oligonucleotides as primers to expand the scope of the analysis.

The comparative analysis of the Vβ repertoire in AIDS patients and in normal controls revealed the existence of important differences in the number of the Vβ genes expressed by the two groups FIG. 1. Expression of the TCR-Vβ genes in T cells from AIDS patients (⊚) and from normal controls(○) is shown in the figure. The results are expressed as absorbance at 450 nm from the DEIA test. The cut-off value was 0.20 and represents the mean value of 10 negative controls ±3 SD. The Vβ14, Vβ15, Vβ16 and Vβ18 sequences could not be detected in any of the cDNAs derived from lymphocytes of HIV+ patients. Similarly, Vβ17, Vβ19 and Vβ20 were found to be expressed in only one of these cDNAs. All other Vβ genes analyzed were randomly represented in HIV+ patient cells.

Figure 2:
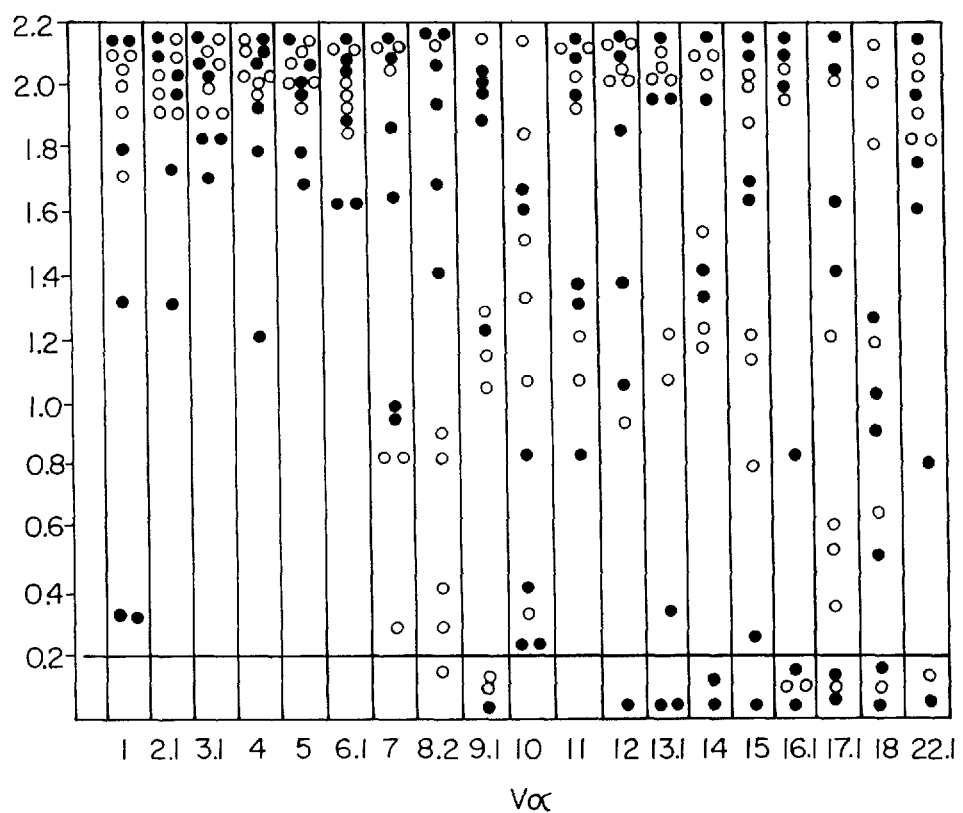
FIG. 2 shows the expression of the T cell receptor Vα genes in T cells from HIV infected individuals and from healthy controls.

The results reported in FIG. 2 demonstrate that there were no major differences between the Vα repertoires of normal individuals and of HIV+ patients. Expression of the TCR-Vβ genes in T cells from AIDS patients (⊚) and from normal controls(○) is shown in the figure, the results are expressed as absorbance at 450 nm from the DEIA test. The cut-off value was 0.20 and represents the mean value of 10 negative controls ±3 SD. Most of the Vα genes were expressed in all samples and there was no evidence of important genomic or somatic deletions. Although the results are only qualitative, due to possible variations in the efficiency of the amplification reactions, it appeared that the relative abundance of the 19 Vα transcripts analyzed was highly variable in both group of samples. These variations are probably correlated to the positive and negative selections processed that occur in the periphery of the immune system.

Example 5

Analysis of the Vβ repertoire by Southern Blot Hybridization

Vβ expression in T cells from individual AIDS patients (group 1 of Table I), and from one healthy control also of Table I, was also analyzed by Southern blot hybridization with a $^{32}$P labeled Cβ-specific probe. After amplification, the layer of mineral oil was removed and aliquots (10 μl) of each amplification reaction were analyzed by electrophoresis in 1% agarose gels. Bands were visualized by ethidium bromide staining and photographed at 302 nm. The expected size of the amplification products obtained was 129 base pairs (bp) for Vα-Cα products and 330 bp for Vβ-Cβ products.

Electrophoresed amplified DNA was transferred to Hybond N nylon blotting membrane (Amersham, Amersham, UK), following the manufacturer's instructions. Filters were incubated for 2 h at 65° C. in prehybridization solution containing 5× SSC (1× SSC: 0.15M NaCl, 0.015M sodium citrate), 5× Denhardt's solution (1× Denhardt's: 0.02% polyvinyl pyrrolidone, 0.02% Ficoll, 0.02% BSA), 0.1% SDS, 100 μg/ml salmon sperm DNA and then hybridized overnight at 42° C. with $^{32}$P-labeled Cβ5′ specific probe at 1×10$^6$ cpm/ml of hybridization solution. The membrane was then washed twice for 10 min at room temperature in 2× SSC, 0.1% SDS and used to expose X-OMAT, XAR X-ray film (Eastman Kodak Co. Rochester, N.Y.).

Figure 3:
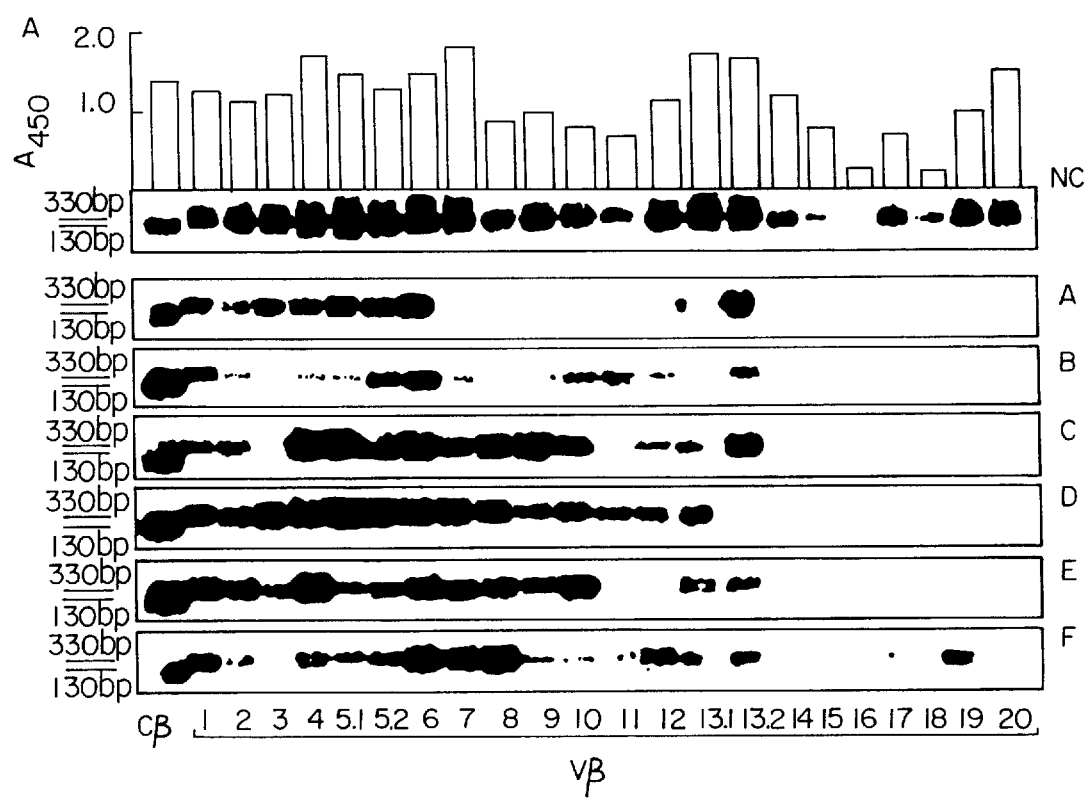
FIG. 3 shows the results of the DEIA assay of the amplified Vβ transcripts obtained with T cells from a control and the results of Southern blot analysis of amplified Cβ and Vβ transcripts obtained with T cells from HIV infected individuals.

The results of the experiment are shown in FIG. 3. FIG. 3A shows the results of the DEIA assay of the amplified TCR-Vβ transcripts obtained with T cell from a normal control. The experiment was carried out as described, using the CβNH$_2$ oligonucleotide shown in Table II as the capture probe. FIG. 3B shows the results of Southern blot analysis of amplified TCR-Vβ and Cβ transcripts obtained with T cells of a control (NC) and from AIDS patients (group 1, Table I).

T cells from the control expressed all the Vβ genes, but there were considerable differences in the level of the individual transcripts. In this sample Vβ15, Vβ16 and Vβ18 were the least expressed, while Vβ5.1 and Vβ13.1 were the most abundant. The Vβ repertoire of the AIDS patients was, in general, more restricted as compared to the normal control, but the degree of this restriction varied considerably among the different samples. Patient B expressed only Vβ1, Vβ5.2 and Vβ6; all other transcripts were either absent or barely detectable. The next most compromised repertoire was the one of patient A, in which we detected only 8 of the 22 transcript tested. Patient D expressed the highest number of Vβ genes but, even in this case, the transcription of 8 Vβ segments could not be detected. The most striking result of this analysis was that, beside the individual variations, all samples lacked the expression of a common set of Vβ genes comprising Vβ14, Vβ15, Vβ16, Vβ17, Vβ18, Vβ19 and Vβ20. The only exception was patient F that expressed Vβ19 and extremely low levels of Vβ17. These results establish that HIV infection results in a severely compromised Vβ repertoire in which members of particular Vβ families are preferentially affected.

Example 6

Vβ mRNA Levels and Disease Progression

Figure 4:
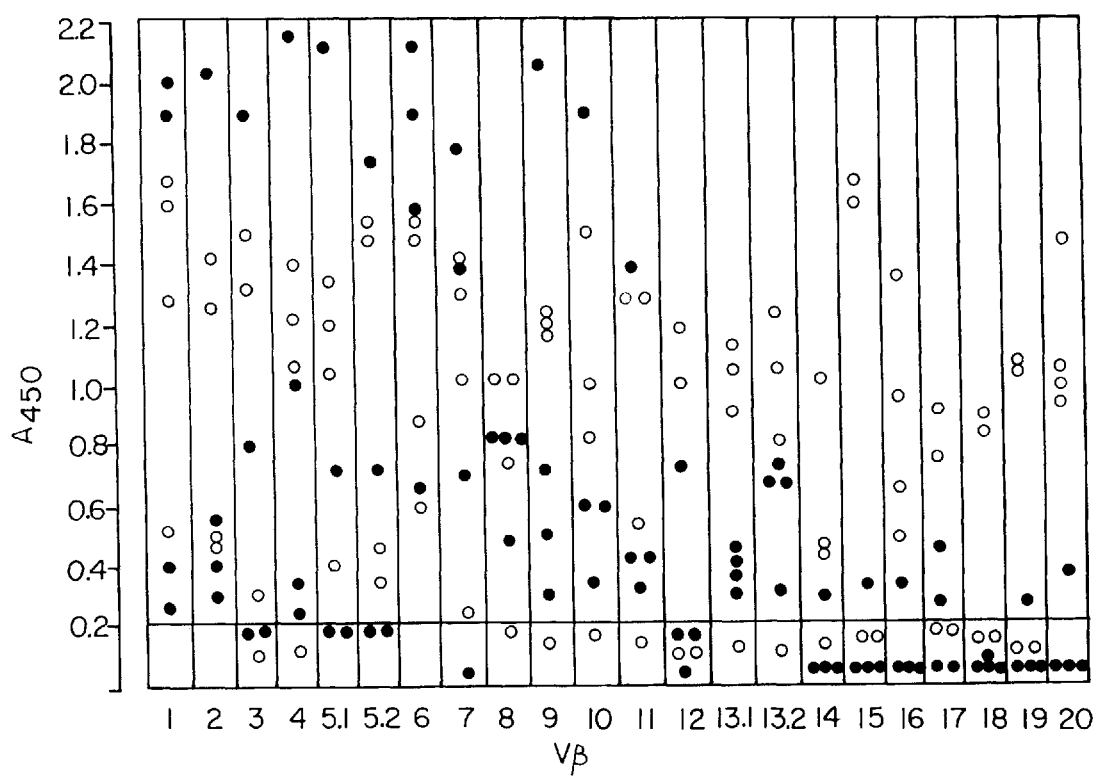
FIG. 4 shows the expression of T cell receptor Vβ genes in T cells from two groups of HIV infected patients at different stages of infection (CDC Stages II and III).
Figure 5A:
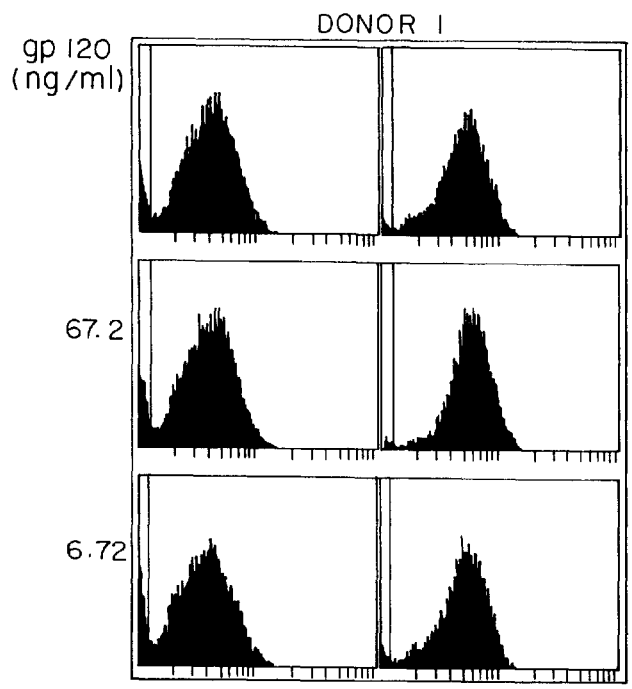
FIG. 5 shows the results of cytofluorimetric analysis of cell surface CD3 and CD4 modulation in four healthy donors, after the stimulation of lymphocytes with a mixture of Staphylococcal enterotoxins B, C2 and E, and an overnight incubation with HIV gp120.
Figure 5B:
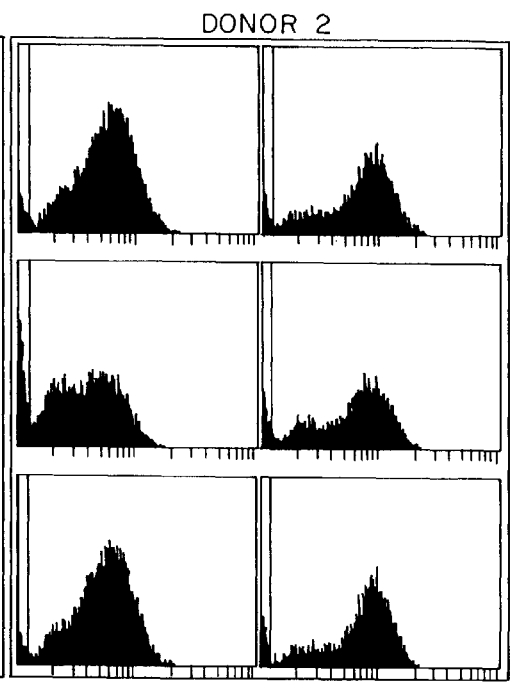
Figure 5C:
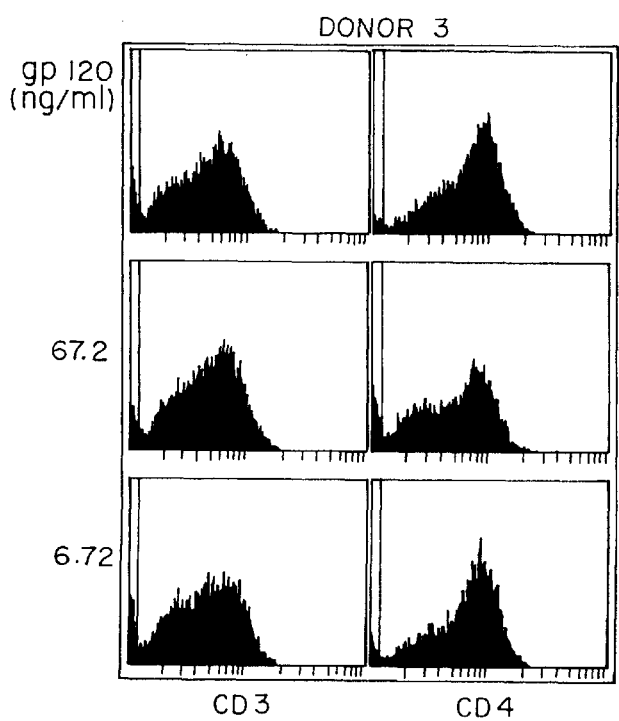
Figure 5D:
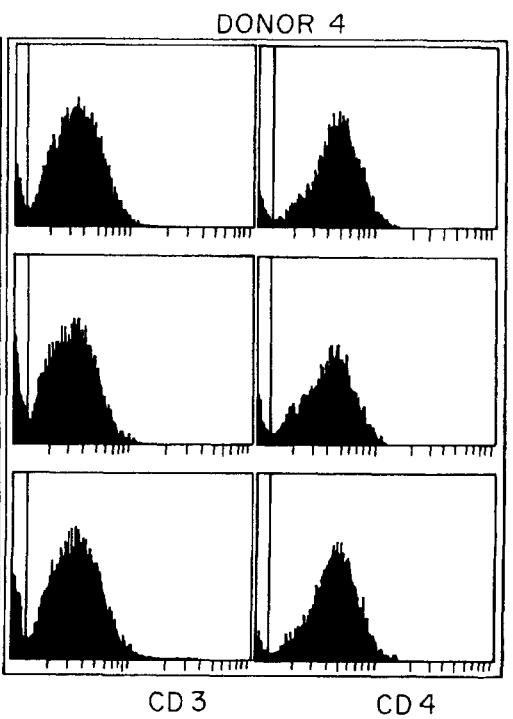

To study whether Vβ extinction correlates with the progression of HIV infection to AIDS, we analyzed the expression of Vβ genes in two other groups of HIV positive patients. Group A consisted of patients with severe immune depletion (CD4<200 mmc), without the occurrence of the clinical manifestation of AIDs syndrome (CDC stage III). Group B consisted of patients with a long history of HIV infection (>5 years) that had retained a normal immunological profile (CDC stage II). The results reported in FIG. 4 show that the two groups display a distinct pattern of Vβ expression. The pattern of the group A (indicated by a "●") patients strongly resembles the one seen in stage IVC1 AIDS patients in which Vβ14, Vβ15, Vβ16, Vβ17, Vβ18, Vβ19 and Vβ20 are either not expressed or barely detectable. Conversely, the group B (indicated by a "○") displayed a pattern of Vβ expression more similar to the one of normal controls, in which most of the Vβ genes were randomly represented.

Example 7

Immunofluorescence Analysis of Cells

Fluorescein-conjugated mAb to CD3 and CD4 (T3 FITC and T4-FITC) were purchased from Coulter Immunology, Hialeah, Fla., and the fluorescein-conjugated anti-TCR-specific antibodies (anti Vβ5, anti-Vβ6, anti-Vβ8 and anti-Vβ12) were purchased from T Cell Diagnostic, Inc., Cambridge, Mass. Staphylococcal enterotoxins E, B and C2 (SEE, SEB and SEC2) were purchased from Serva Feinbiochemica, GmbH & Co. Heidelberg.

Peripheral blood mononuclear cells (PBMC) were prepared from heparinized human peripheral blood samples from clinically healthy donors as in Example 1. Cells were placed at a concentration of 2×10⁶/ml on petri dishes coated either with 100 ng/ml of T3 mAb or with 10 ng/ml of SEE, 50 ng/ml of SEC2 and 100 ng/mnl of SEB. The enterotoxin SEB is known to stimulate T cells positive for Vβ3, Vβ12, Vβ14, Vβ15, Vβ17, and Vβ20; SEC2 is known to stimulate T cells positive for Vβ12, Vβ13.1, Vβ13.2, Vβ14, Vβ15, Vβ17, and Vβ20; and SEE is known to stimulate T cells positive for Vβ5.1, Vβ6.1, Vβ6.2, Vβ6.3, Vβ8, and Vβ18. After 3 days of culturing, the activated cells were washed and incubated overnight with or without two doses (67.2 and 6.72 ng/ml) of insolubilized gp120 (Transgene, Stranbourg) in RPMI 1640 (GIBCO Laboratories, Grand Island, N.Y.). In another series of experiments 2×10⁶ lymphocytes were preincubated overnight with 67.2 ng/ml of gp120 and then for 4 or 5 days with SEE (10 ng/ml), SEC2 (50 ng/ml) or SEB (100 ng/ml).

For staining, 5×10⁵ blasts (ie. PBMCs activated by enterotoxins SEB, SEC2, or SEE) in 100 μl of PBS, 2% FC3, were incubated for 30 min. at 1° C. with FITC-conjugated anti-CD3, anti-CD4, anti-CD8, and anti-TCR mAbs. All samples were analyzed on a EPICS C flow cytometer (Coulter) gated to exclude non viable cells. 2×10⁴ viable cells were accumulated for histograms using logarithmic amplification of fluorescence intensity. Data are presented as percentage of positive cells after subtraction of background staining with the fluorescent anti Ig reagent. Unstained cells or cells stained with FITC-GαM Ig (Fab')₂ (Technogenetics, Trezzano sul Naviglio, Italy) were used as negative controls.

PBMCs from healthy individuals were first activated with the superantigens SEB, SEC2 and SEE that selectively expand those cells bearing Vβ regions for which specific monoclonal antibodies are available. After 3 days of culturing the activated cells were washed and incubated overnight with or without various doses of insolubilized gp120. Flow cytometric analysis with fluorescein-labeled antibodies specific to CD3, CD4, Vβ5, Vβ6, Vβ8 and Vβ12 revealed that preincubation with gp120 did not change the membrane expression of CD3 and CD4 (FIG. 5), but resulted in membrane down-modulation of some, but not all, Vβ segments and that the phenomenon was strictly dependent on the concentration of gp120 added to the cultures (FIG. 6). Different Vβ segments were modulated in cell samples deriving from different donors, suggesting that polymorphic structures may be involved in this interaction.

Figure 7:
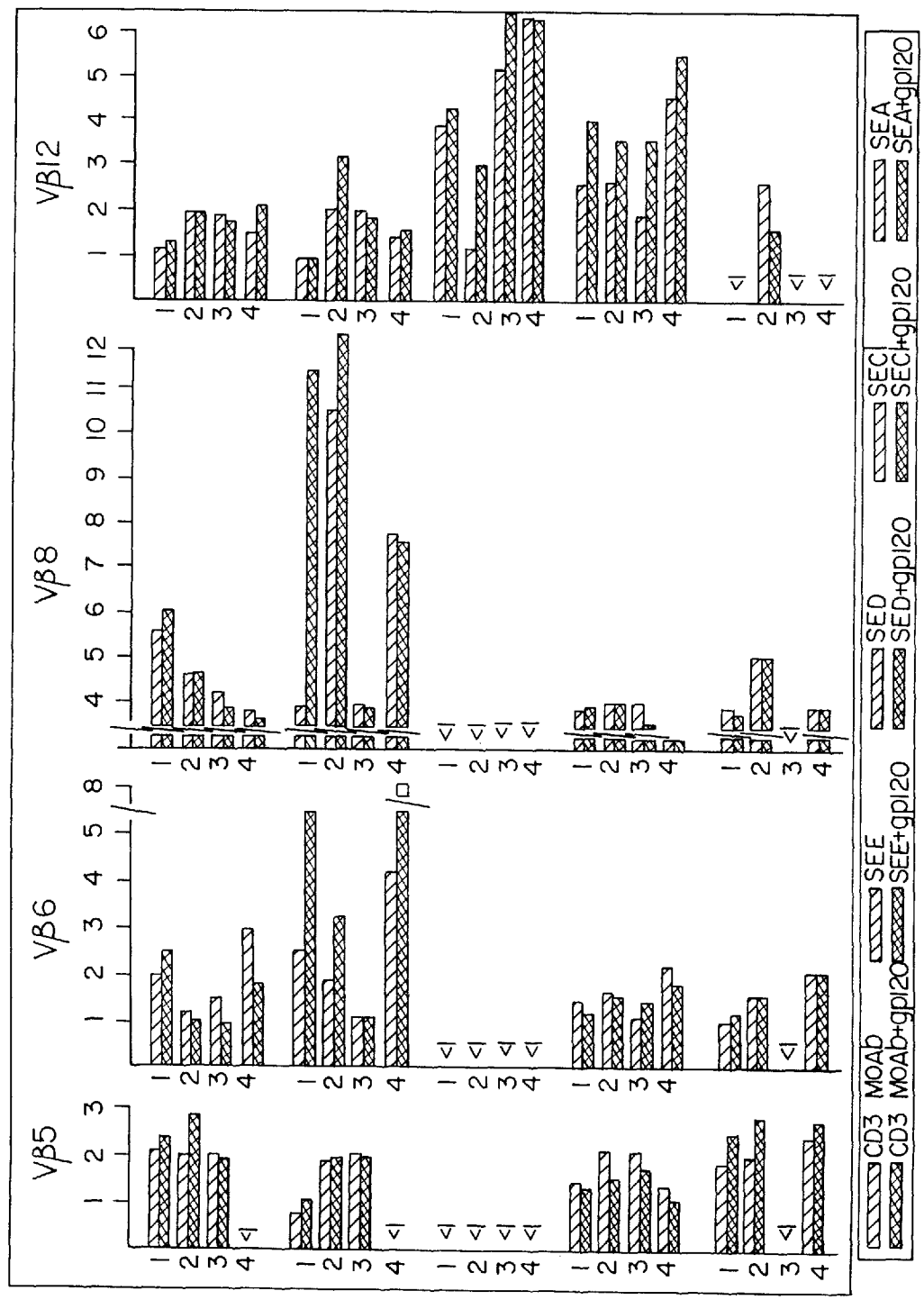
FIG. 7 shows the results of cytofluorimetric analysis of cell surface Vβ5, Vβ6, Vβ8 and Vβ12 expression in four healthy donors, after an overnight incubation of lymphocytes with two doses of HIV gp120 and a subsequent stimulation of the cells with a mixture of Staphylococcal enterotoxins B, C2 and E.

In a second series of experiments PBMC were first incubated overnight with or without gp120 and, after washing, recultured for five days in the presence of SEB, SEC2, SEE. Flow cytometric analysis using fluoresceined anti-Vβ antibodies revealed that, in some samples, preincubation with gp120 favored the expansion of those cells bearing Vβ6 and Vβ8 but not of those bearing Vβ5 and Vβ12 (FIG. 7). Taken together, these observations suggest that only some Vβ segments may act as a co-receptor for gp120.

Example 8

Autoimmunity and TCR-Vβ Components

Figure 8A:
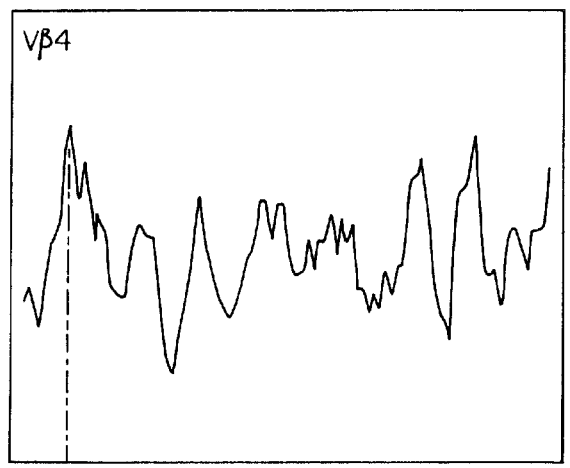
FIG. 8 shows the calculated hydropathic profiles of deduced amino acid sequences of the Vβ4, Vβ19 and Vβ20 peptides.
Figure 8B:
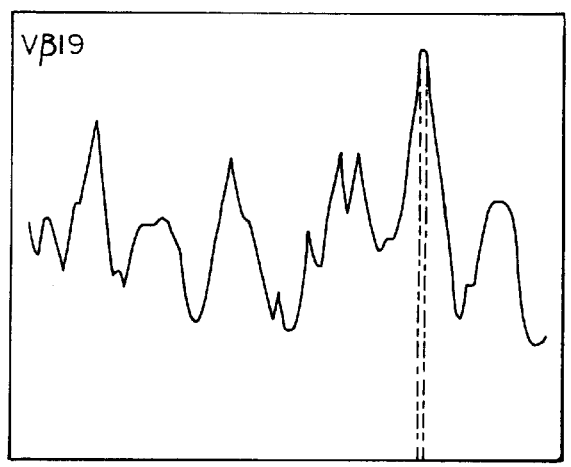
Figure 8C:
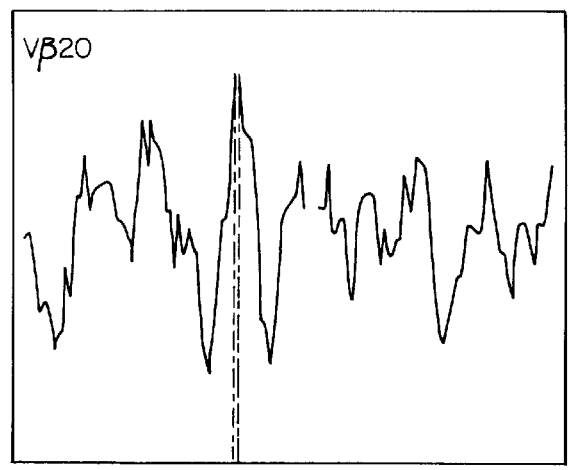

A comparison of the amino acid sequences of gp120 and the known human TCR segments carried out in our laboratories has revealed that gp120 shares common motifs with some Vβ genes. Some of these motifs map in the most potentially antigenic region of the relevant Vβ segments. On the basis of this evidence we constructed a first series of peptides corresponding to the putative immunogenic regions of Vβ4 (Ser-Ala-Val-Ile-Ser-Gln-Lys-Pro-Ser-Arg-Asp-Ile- Cys-Gln-Arg-Gly-Thr-Ser-Leu-Thr), Vβ19 (Gln-Leu-Gln-Glu-Thr-Glu-Asn-His-Lys-Lys-Arg-Phe-Ser-Ser-Gln-Cys-Pro) and Vβ20 (Gln-Asn-Leu-Ser-Ala-Ser-Arg-Pro-Gln-Asp-Arg-Gln-Phe-Ile-Leu-Ser-Ser-Lys). These peptides can be found in the region of greatest peptide hydrophilicity for each of the corresponding peptides (FIG. 8). The choice of these immunodominant epitopes of these TCR Vβ peptides was done with the aid of a computer program (PCGENE; Intelligenetics) using the Hopp and Wood algorithm. Alternatively, one could construct the following series of peptides for use in the present invention: Vβ12 (Asp-Gly-Tyr-Ser-Val-Ser-Arg-Ser-Lys-Thr-Glu-Asp-Phe-Leu-Leu), Vβ15 (Pro-Arg-Asn-Arg-Ile-Thr-Lys-Ile-Gly-Lys-Arg-Ile-Met-Leu-Glu-Cys), and Vβ18 (Pro-Arg-His-Leu-Val-Arg-Arg-Arg-Gly-Gln-Glu-Ala-Arg-Leu-Arg-Cys).

The peptides were synthetized by solid phase peptide synthesis now described. A polyamidic resin, functionalized with the C-terminal amino acid (0.1 meq/g), was used as solid support. All of the amino acids were pentafluorophenyl esters preactivated and protected at the α-amino group with 9-fluorenilmethoxycarbonyl (Fmoc) and in the lateral chains according to the nature of specific amino acid, 1-hydroxybenzothriazole (HOBT) was used as catalyst and each coupling was conducted in dimethyl formamide (DMF) with a 5 fold excess of amino acid for 2 hours. DMF was used for wash and 20% piperidine/DMF for the deprotection of the α-amino groups. At the end of synthesis the resin was washed successively with DMF, glacial acetic acid, tort-amylic alcohol, dietyl ether and dessicated. The peptide was cleaved from the resin with a mixture of trifluoroacetic acid (TFA) and scavengers (anisole, phenol, ethandiol (EDT)) for 2 hours at room temperature (94% TFA, 5% anisole and 1% EDT for Vβ4, Vβ15, Vβ18, and Vβ19; 95% TFA and 5% phenol for Vβ12 and Vβ20). The resin was separated from the solution by filtration, the filtrate was evaporated and the slurry obtained was precipitated with diethyl ether. The product was repeatedly washed with diethyl ether, then dissolved in glacial acetic acid and lyophilized. The peptides were purified by RP-HPLC on a C18 column with a gradient of water and acetonitrile both containing 0.1% TFA. The composition of the peptides was controlled by amino acid analysis with phenylisothiocyanate (PITC) pre-column derivatization.

The sera of AIDS patients (CDC stage: IV) and healthy HIV-individuals were then tested for immunoreactivity against this first series of peptides. Microtiter dishes were coated by treating with 200 μl of a 5 μg/ml peptide solution in 0.05M carbonate buffer, pH 9.6 for one hour at 37° C. The peptide solution was then removed and the wells overcoated with 300 μl of 0.2% BSA in 0.1M Tris.HCl buffer, pH 7.4 for two hours at room temperature. The wells were then fixed with 300 μl of 10% saccharose, 4% PVP, 9% NaCl in water for one hour at room temperature. The fix solution was removed and the wells dessicated at room temperature overnight. The various sera were diluted 1/50 in PBS/10% FCS and 200 μl of the diluted sera were added to wells for one hour at 37° C. The sera were then removed and the wells washed with "wash buffer" from ETI-Kits (Sorin Biomedica; Saluggia, Italy). Polyclonal anti-human Ig-peroxidase conjugated was diluted 1/3000 in PBS/10% FCS and 200 μl aliquots were added to the wells for one hour at 37° C. The wells were then washed three times with "wash buffer". Chromogen-substrate (100 μl, diluted 1:1 according to instructions) was added in the dark and allowed to incubate for 30 minutes at room temperature. The reaction was stopped with 0.1M sulphuric acid.

Figure 9A:
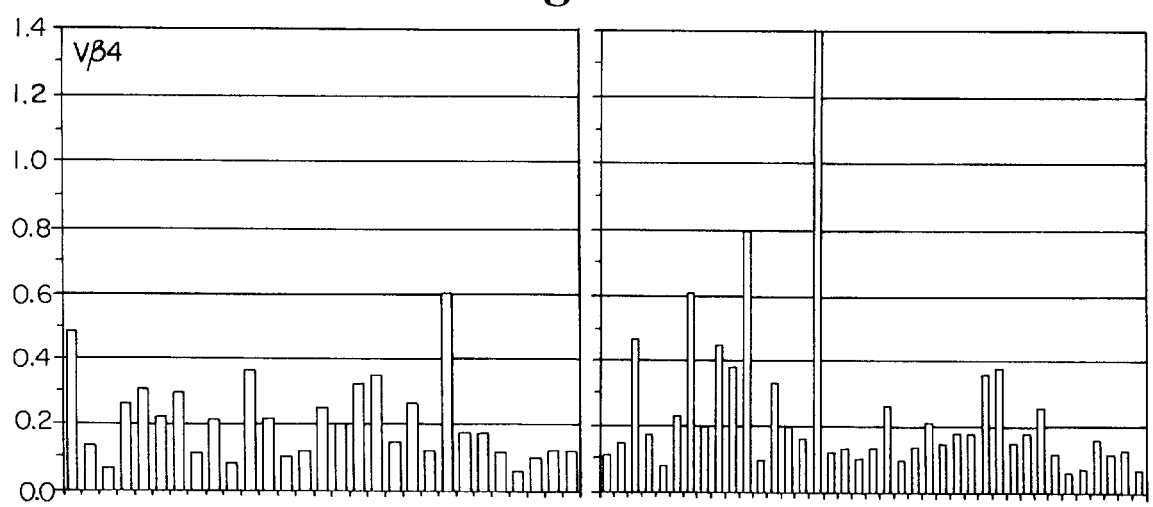
FIG. 9 shows the immune reactivity of sera obtained from normal donors and from HIV-infected patients at CDC stage IV against the immunodominant fragments of Vβ4, Vβ19 and Vβ20 peptides.
Figure 9B:
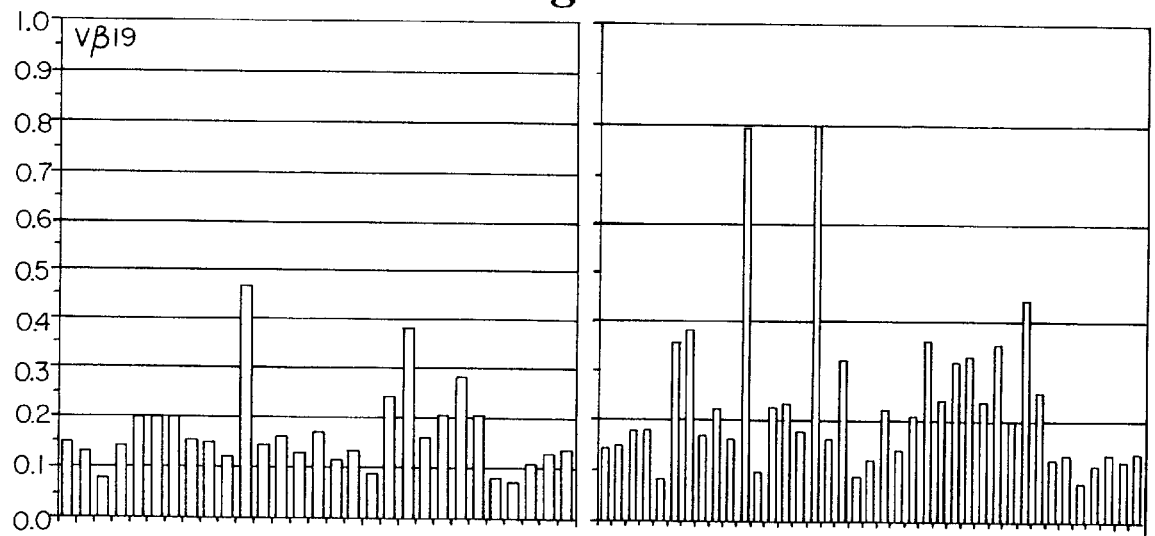
Figure 9C:
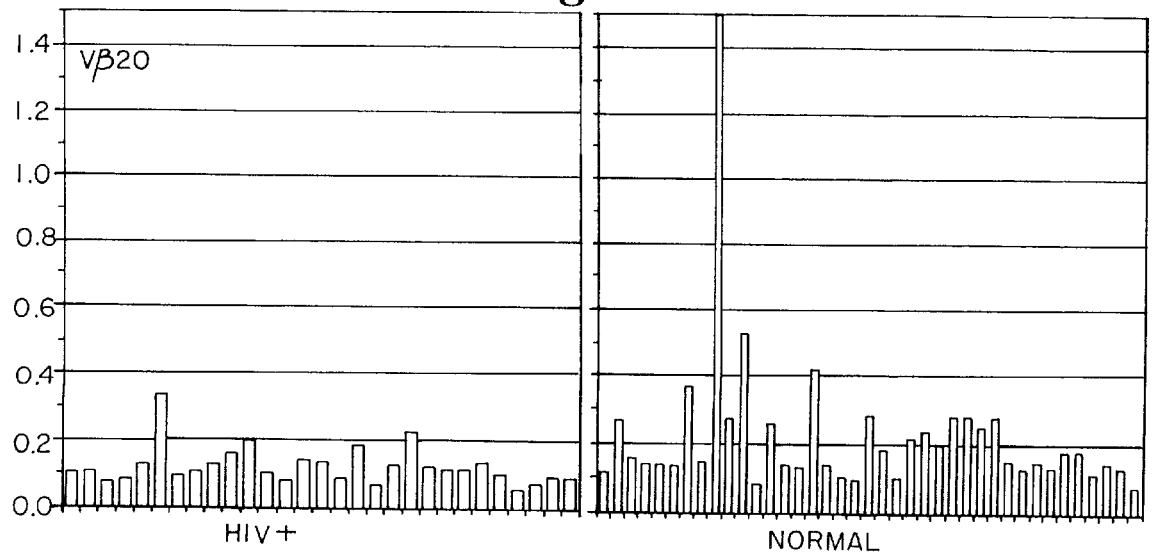

The results of the tests are shown in FIG. 9. Immunoreactivity of sera obtained from normal donors (right) and from HIV-infected patients (left) against the immonodominant peptides of 4, 19, and 20 is shown. Immunoreactivity against these peptides is found preferentially in the sera of AIDS patients. The specificity of these reactions was verified by inhibition experiments with the homologous peptides.

What is claimed is:

1. A method of assaying an antibody containing fluid of a person infected with HIV comprising:

(a) isolating a sample from the person infected with HIV, said sample suspected to contain an antibody having a paratope specific to an epitope on a TCR-Vβ;
   (b) preparing the sample for contact with a binding agent specific to the paratope of the antibody;
   (c) contacting the prepared sample with the binding agent under conditions suitable for binding of the antibody with the binding agent;
   (d) determining the extent of binding; and
   (e) correlating the extent of binding to the presence or amount of said antibody in said fluid.

2. The method of claim 1 wherein the paratope of the antibody is also specific to an epitope on gp120 of HIV.

3. The method of claim 1 wherein the binding agent is a member selected from the group consisting of an antibody, an antibody fragment, a binding receptor, a binding receptor fragment and a polypeptide containing fewer than 100 amino acids.

4. A method of assaying an antibody containing fluid of a person infected with HIV comprising:

(a) isolating a sample from the person infected with HIV, said sample suspected to contain an antibody having a paratope specific to an epitope on a TCR-Vβ;
   (b) preparing the sample for contact with a binding agent specific to the paratope of the antibody;
   (c) contacting the prepared sample with the binding agent under conditions suitable for binding of the antibody with the binding agent;
   (d) determining the extent of binding; and
   (e) correlating the extent of binding to the presence or amount of said antibody in said fluid, wherein the paratope of the antibody is specific to an epitope on an amino acid sequence, the amino acid sequence being selected from the group consisting of:
   Ser-Ala-Val-Ile-Ser-Gln-Lys-Pro-Ser-Arg-Asp-Ile-Cys-Gln-Arg-Gly-Thr-Ser-Leu-Thr (SEQ ID NO: 28);
   Gln-Leu-Gln-Glu-Thr-Glu-Asn-His-Lys-Lys-Arg-Phe-Ser-Ser-Gln-Cys-Pro (SEQ ID NO: 29);
   Gln-Asn-Leu-Ser-Ala-Ser-Arg-Pro-Gln-Asp-Arg-Gln-Phe-Ile-Leu-Ser-Ser-Lys (SEQ ID NO: 30);
   Asp-Gly-Tyr-Ser-Val-Ser-Arg-Ser-Lys-Thr-Glu-Asp-Phe-Leu-Leu (SEQ ID NO: 31);
   Pro-Arg-Asn-Arg-Ile-Thr-Lys-Ile-Gly-Lys-Arg-Ile-Met-Leu-Glu-Cys (SEQ ID NO: 32); and
   Pro-Arg-His-Leu-Val-Arg-Arg-Arg-Gly-Gln-Glu-Ala-Arg-Leu-Arg-Cys (SEQ ID NO: 33).

5. A method of assaying an antibody containing fluid of a person infected with HIV comprising:

(a) isolating a sample from the person infected with HIV, said sample suspected to contain an antibody having a paratope specific to an epitope on a TCR-Vβ;
   (b) preparing the sample for contact with a binding agent specific to the paratope of the antibody;
   (c) contacting the prepared sample with the binding agent under conditions suitable for binding of the antibody with the binding agent;

(d) determining the extent of binding; and (e) correlating the extent of binding to the presence or amount of said antibody in said fluid, wherein the paratope of the antibody is specific to an epitope on a TCR-Vβ selected from the group consisting of TCR-Vβ14, TCR-Vβ15, TCR-Vβ16, TCR-Vβ17, TCR-Vβ18, TCR-Vβ19, and TCR-Vβ20.

6. The method of claim 1 wherein the paratope of the antibody is specific to an epitope on a TCR-Vβ selected from the group consisting of TCR-Vβ4, TCR-Vβ12, TCR-Vβ15, TCR-Vβ18, TCR-Vβ19 and TCR-Vβ20.

* * * * *

SEQUENCE LISTING ( 1 ) GENERAL INFORMATION:

( i i i ) NUMBER OF SEQUENCES: 57

( 2 ) INFORMATION FOR SEQ ID NO: 1:

( i ) SEQUENCE CHARACTERISTICS:
        ( A ) LENGTH: 18 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini, Alessandra; Bettinardi, Alessandra; Puoti, Massimo; Primi, Daniele
        ( B ) TITLE: Selective Depletion in HIV Infection of T Cells That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 1:

GTGCACCTCC TTCCCATT                                          1 8

( 2 ) INFORMATION FOR SEQ ID NO: 2:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini, Alessandra; Bettinardi, Alessandra; Puoti, Massimo; Primi, Daniele
        ( B ) TITLE: Selective Depletion in HIV Infection of T Cells That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 2:

GCACAACAGT TCCCTGACTT GCAC                                  2 4

( 2 ) INFORMATION FOR SEQ ID NO: 3:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using
        oligonucleotide synthesis machine ( x ) PUBLICATION INFORMATION:
        ( A ) AUTHORS: Imberti, Luisa; Sottini,
            Alessandra; Bettinardi, Alessandra; Puoti, Massimo;
            Primi, Daniele
        ( B ) TITLE: Selective Depletion in HIV Infection
            of T Cells That Bear Specific T Cell Receptor Vb
            Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 3:

```
TCATCAACCA TGCAAGCCTG ACCT                                          24
```

( 2 ) INFORMATION FOR SEQ ID NO: 4:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using
        oligonucleotide synthesis machine ( x ) PUBLICATION INFORMATION:
        ( A ) AUTHORS: Imberti, Luisa; Sottini,
            Alessandra; Bettinardi, Alessandra; Puoti, Massimo;
            Primi, Daniele
        ( B ) TITLE: Selective Depletion in HIV Infection
            of T Cells That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 4:

```
GTCTCTAGAG AGAAGAAGGA GCGC                                          24
```

( 2 ) INFORMATION FOR SEQ ID NO: 5:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid (oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
- ( A ) AUTHORS: Imberti, Luisa; Sottini, Alessandra; Bettinardi, Alessandra; Puoti, Massimo; Primi, Daniele
- ( B ) TITLE: Selective Depletion in HIV Infection of T Cells That Bear Specific T Cell Receptor Vb Sequences
- ( C ) JOURNAL: Science
- ( D ) VOLUME: 254
- ( E ) ISSUE: 5033
- ( F ) PAGES: 860-862
- ( J ) PUBLICATION DATE: November 8, 1991

( x i ) SEQUENCE DESCRIPTION: SEQ ID NO: 5:

ACATATGAGA GTGGATTTGT CATT 24

( 2 ) INFORMATION FOR SEQ ID NO: 6:

( i ) SEQUENCE CHARACTERISTICS:
- ( A ) LENGTH: 25 bases
- ( B ) TYPE: Nucleic Acid
- ( C ) STRANDEDNESS: Single
- ( D ) TOPOLOGY: Linear ( i i ) MOLECULE TYPE: Other nucleic acid
(oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
- ( A ) AUTHORS: Imberti, Luisa; Sottini, Alessandra; Bettinardi, Alessandra; Puoti, Massimo; Primi, Daniele
- ( B ) TITLE: Selective Depletion in HIV Infection of T Cells That Bear Specific T Cell Receptor Vb Sequences
- ( C ) JOURNAL: Science
- ( D ) VOLUME: 254
- ( E ) ISSUE: 5033
- ( F ) PAGES: 860-862
- ( J ) PUBLICATION DATE: November 8, 1991

( x i ) SEQUENCE DESCRIPTION: SEQ ID NO: 6:

ATACTTCAGT GAGACACAGA GAAAC 25

( 2 ) INFORMATION FOR SEQ ID NO: 7:

( i ) SEQUENCE CHARACTERISTICS:
- ( A ) LENGTH: 24 bases
- ( B ) TYPE: Nucleic Acid
- ( C ) STRANDEDNESS: Single
- ( D ) TOPOLOGY: Linear ( i i ) MOLECULE TYPE: Other nucleic acid
(oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
- ( A ) AUTHORS: Imberti, Luisa; Sottini, Alessandra; Bettinardi, Alessandra; Puoti, Massimo; Primi, Daniele (B) TITLE: Selective Depletion in HIV Infection of T Cells
    That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 7:

TTCCCTAACT ATAGCTCTGA GCTG    24

(2) INFORMATION FOR SEQ ID NO: 8:

(i) SEQUENCE CHARACTERISTICS:
    (A) LENGTH: 20 bases
    (B) TYPE: Nucleic Acid
    (C) STRANDEDNESS: Single
    (D) TOPOLOGY: Linear (ii) MOLECULE TYPE: Other nucleic acid
    (oligonucleotide useful in amplification of T Cell Receptor Vb region)

(iii) HYPOTHETICAL: No (v) ORIGINAL SOURCE: Synthesized using oligonucleotide synthesis machine (x) PUBLICATION INFORMATION:
    (A) AUTHORS: Imberti, Luisa; Sottini,
        Alessandra; Bettinardi, Alessandra; Puoti, Massimo; Primi,
        Daniele
    (B) TITLE: Selective Depletion in HIV Infection of T Cells
        That Bear Specific T Cell Receptor Vb Sequences
    (C) JOURNAL: Science
    (D) VOLUME: 254
    (E) ISSUE: 5033
    (F) PAGES: 860-862
    (J) PUBLICATION DATE: November 8, 1991

(xi) SEQUENCE DESCRIPTION: SEQ ID NO: 8:

AGGCCTGAGG GATCCGTCTC    20

(2) INFORMATION FOR SEQ ID NO: 9:

(i) SEQUENCE CHARACTERISTICS:
    (A) LENGTH: 22 bases
    (B) TYPE: Nucleic Acid
    (C) STRANDEDNESS: Single
    (D) TOPOLOGY: Linear (ii) MOLECULE TYPE: Other nucleic acid
    (oligonucleotide useful in amplification of T Cell Receptor Vb region)

(iii) HYPOTHETICAL: No (v) ORIGINAL SOURCE: Synthesized using oligonucleotide synthesis machine (x) PUBLICATION INFORMATION:
    (A) AUTHORS: Imberti, Luisa; Sottini,
        Alessandra; Bettinardi, Alessandra; Puoti, Massimo;
        Primi, Daniele
    (B) TITLE: Selective Depletion in HIV Infection of T Cells
        That Bear Specific T Cell Receptor Vb Sequences
    (C) JOURNAL: Science
    (D) VOLUME: 254
    (E) ISSUE: 5033
    (F) PAGES: 860-862
    (J) PUBLICATION DATE: November 8, 1991

(xi) SEQUENCE DESCRIPTION: SEQ ID NO: 9:

CCTGAATGCC CCAACAGCTC TC    22

( 2 ) INFORMATION FOR SEQ ID NO: 10:

( i ) SEQUENCE CHARACTERISTICS:
( A ) LENGTH: 24 bases
( B ) TYPE: Nucleic Acid
( C ) STRANDEDNESS: Single
( D ) TOPOLOGY: Linear ( i i ) MOLECULE TYPE: Other nucleic acid
(oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
( A ) AUTHORS: Imberti, Luisa; Sottini, Alessandra; Bettinardi, Alessandra; Puoti, Massimo; Primi, Daniele
( B ) TITLE: Selective Depletion in HIV Infection of T Cells That Bear Specific T Cell Receptor Vb Sequences
( C ) JOURNAL: Science
( D ) VOLUME: 254
( E ) ISSUE: 5033
( F ) PAGES: 860-862
( J ) PUBLICATION DATE: November 8, 1991

( x i ) SEQUENCE DESCRIPTION: SEQ ID NO: 10:

ATTTACTTTA ACAACAACGT TCCG 24

( 2 ) INFORMATION FOR SEQ ID NO: 11:

( i ) SEQUENCE CHARACTERISTICS:
( A ) LENGTH: 24 bases
( B ) TYPE: Nucleic Acid
( C ) STRANDEDNESS: Single
( D ) TOPOLOGY: Linear ( i i ) MOLECULE TYPE: Other nucleic acid
(oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
( A ) AUTHORS: Imberti, Luisa; Sottini, Alessandra; Bettinardi, Alessandra; Puoti, Massimo; Primi, Daniele
( B ) TITLE: Selective Depletion in HIV Infection of T Cells That Bear Specific T Cell Receptor Vb Sequences
( C ) JOURNAL: Science
( D ) VOLUME: 254
( E ) ISSUE: 5033
( F ) PAGES: 860-862
( J ) PUBLICATION DATE: November 8, 1991

( x i ) SEQUENCE DESCRIPTION: SEQ ID NO: 11:

CCTAAATCTC CAGACAAAGC TCAC 24

( 2 ) INFORMATION FOR SEQ ID NO: 12:

( i ) SEQUENCE CHARACTERISTICS:
( A ) LENGTH: 24 bases
( B ) TYPE: Nucleic Acid
( C ) STRANDEDNESS: Single
( D ) TOPOLOGY: Linear ( i i ) MOLECULE TYPE: Other nucleic acid
(oligonucleotide useful in amplification of T Cell Receptor Vb region)

(i i i) HYPOTHETICAL: No (v) ORIGINAL SOURCE: Synthesized using oligonucleotide synthesis
machine (x) PUBLICATION INFORMATION:
(A) AUTHORS: Imberti, Luisa; Sottini,
Alessandra; Bettinardi, Alessandra; Puoti, Massimo;
Primi, Daniele
(B) TITLE: Selective Depletion in HIV Infection of T Cells
That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(x i) SEQUENCE DESCRIPTION: SEQ ID NO: 12:

CTCCAAAAAC TCATCCTGTA CCTT                                                  24

(2) INFORMATION FOR SEQ ID NO: 13:

(i) SEQUENCE CHARACTERISTICS:
(A) LENGTH: 24 bases
(B) TYPE: Nucleic Acid
(C) STRANDEDNESS: Single
(D) TOPOLOGY: Linear (i i) MOLECULE TYPE: Other nucleic acid
(oligonucleotide useful in amplification of T Cell Receptor Vb
region)

(i i i) HYPOTHETICAL: No (v) ORIGINAL SOURCE: Synthesized using oligonucleotide synthesis
machine (x) PUBLICATION INFORMATION:
(A) AUTHORS: Imberti, Luisa; Sottini,
Alessandra; Bettinardi, Alessandra; Puoti, Massimo;
Primi, Daniele
(B) TITLE: Selective Depletion in HIV Infection of T Cells
That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(x i) SEQUENCE DESCRIPTION: SEQ ID NO: 13:

TCAACAGTCT CCAGAATAAG GACG                                                  24

(2) INFORMATION FOR SEQ ID NO: 14:

(i) SEQUENCE CHARACTERISTICS:
(A) LENGTH: 18 bases
(B) TYPE: Nucleic Acid
(C) STRANDEDNESS: Single
(D) TOPOLOGY: Linear (i i) MOLECULE TYPE: Other nucleic acid
(oligonucleotide useful in amplification of T Cell Receptor Vb
region)

(i i i) HYPOTHETICAL: No (v) ORIGINAL SOURCE: Synthesized using oligonucleotide synthesis
machine (x) PUBLICATION INFORMATION:
(A) AUTHORS: Imberti, Luisa; Sottini,
Alessandra; Bettinardi, Alessandra; Puoti, Massimo;
Primi, Daniele
(B) TITLE: Selective Depletion in HIV Infection of T Cells
That Bear Specific T Cell Receptor Vb Sequences (C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 14:

AAAGGAGAAG TCTCAGAT                               18

(2) INFORMATION FOR SEQ ID NO: 15:

(i) SEQUENCE CHARACTERISTICS:
(A) LENGTH: 18 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Vb region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi, Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 15:

CAAGGAGAAG TCCCCAAT                               18

(2) INFORMATION FOR SEQ ID NO: 16:

(i) SEQUENCE CHARACTERISTICS:
(A) LENGTH: 18 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Vb region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi, Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 16:

GGTGAGGGTA CAACTGCC                               18

(2) INFORMATION FOR SEQ ID NO: 17:

( i ) SEQUENCE CHARACTERISTICS:
    ( A ) LENGTH: 24 bases
    ( B ) TYPE: Nucleic Acid
    ( C ) STRANDEDNESS: Single
    ( D ) TOPOLOGY: Linear ( i i ) MOLECULE TYPE: Other nucleic acid
    (oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
    ( A ) AUTHORS: Imberti, Luisa; Sottini, Alessandra; Bettinardi, Alessandra; Puoti, Massimo; Primi, Daniele
    ( B ) TITLE: Selective Depletion in HIV Infection of T Cells That Bear Specific T Cell Receptor Vb Sequences
    ( C ) JOURNAL: Science
    ( D ) VOLUME: 254
    ( E ) ISSUE: 5033
    ( F ) PAGES: 860-862
    ( J ) PUBLICATION DATE: November 8, 1991

( x i ) SEQUENCE DESCRIPTION: SEQ ID NO: 17:

```
GTCTCTCGAA AAGAGAAGAG GAAT                                          24
```

( 2 ) INFORMATION FOR SEQ ID NO: 18:

( i ) SEQUENCE CHARACTERISTICS:
    ( A ) LENGTH: 24 bases
    ( B ) TYPE: Nucleic Acid
    ( C ) STRANDEDNESS: Single
    ( D ) TOPOLOGY: Linear ( i i ) MOLECULE TYPE: Other nucleic acid
    (oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
    ( A ) AUTHORS: Imberti, Luisa; Sottini, Alessandra; Bettinardi, Alessandra; Puoti, Massimo; Primi, Daniele
    ( B ) TITLE: Selective Depletion in HIV Infection of T Cells That Bear Specific T Cell Receptor Vb Sequences
    ( C ) JOURNAL: Science
    ( D ) VOLUME: 254
    ( E ) ISSUE: 5033
    ( F ) PAGES: 860-862
    ( J ) PUBLICATION DATE: November 8, 1991

( x i ) SEQUENCE DESCRIPTION: SEQ ID NO: 18:

```
AGTGTCTCTC GACAGGCACA GGCT                                          24
```

( 2 ) INFORMATION FOR SEQ ID NO: 19:

( i ) SEQUENCE CHARACTERISTICS:
    ( A ) LENGTH: 24 bases
    ( B ) TYPE: Nucleic Acid
    ( C ) STRANDEDNESS: Single
    ( D ) TOPOLOGY: Linear ( i i ) MOLECULE TYPE: Other nucleic acid
    (oligonucleotide useful in amplification of T Cell Receptor Vb region)

( i i i ) HYPOTHETICAL: No ( v ) ORIGINAL SOURCE: Synthesized using oligonucleotide synthesis machine
            (x) PUBLICATION INFORMATION:
                (A) AUTHORS: Imberti, Luisa; Sottini,
                    Alessandra; Bettinardi, Alessandra; Puoti, Massimo; Primi,
                    Daniele
                (B) TITLE: Selective Depletion in HIV Infection of T Cells
                    That Bear Specific T Cell Receptor Vb Sequences
                (C) JOURNAL: Science
                (D) VOLUME: 254
                (E) ISSUE: 5033
                (F) PAGES: 860-862
                (J) PUBLICATION DATE: November 8, 1991

(xi) SEQUENCE DESCRIPTION: SEQ ID NO: 19:

AAAGAGTCTA AACAGGATGA GTCC                                                                                          24

(2) INFORMATION FOR SEQ ID NO: 20:

(i) SEQUENCE CHARACTERISTICS:
                (A) LENGTH: 21 bases
                (B) TYPE: Nucleic Acid
                (C) STRANDEDNESS: Single
                (D) TOPOLOGY: Linear (ii) MOLECULE TYPE: Other nucleic acid
                (oligonucleotide useful in amplification of T Cell Receptor Vb
                region)

(iii) HYPOTHETICAL: No (v) ORIGINAL SOURCE: Synthesized using oligonucleotide synthesis
                machine (x) PUBLICATION INFORMATION:
                (A) AUTHORS: Imberti, Luisa; Sottini,
                    Alessandra; Bettinardi, Alessandra; Puoti, Massimo; Primi,
                    Daniele
                (B) TITLE: Selective Depletion in HIV Infection of T Cells
                    That Bear Specific T Cell Receptor Vb Sequences
                (C) JOURNAL: Science
                (D) VOLUME: 254
                (E) ISSUE: 5033
                (F) PAGES: 860-862
                (J) PUBLICATION DATE: November 8, 1991

(xi) SEQUENCE DESCRIPTION: SEQ ID NO: 20:

CAGATAGTAA ATGACTTTCA G                                                                                              21

(2) INFORMATION FOR SEQ ID NO: 21:

(i) SEQUENCE CHARACTERISTICS:
                (A) LENGTH: 24 bases
                (B) TYPE: Nucleic Acid
                (C) STRANDEDNESS: Single
                (D) TOPOLOGY: Linear (ii) MOLECULE TYPE: Other nucleic acid
                (oligonucleotide useful in amplification of T Cell Receptor
                Vb region)

(iii) HYPOTHETICAL: No (v) ORIGINAL SOURCE: Synthesized using
                            oligonucleotide synthesis machine (x) PUBLICATION INFORMATION:
                (A) AUTHORS: Imberti, Luisa; Sottini,
                    Alessandra; Bettinardi, Alessandra; Puoti, Massimo; Primi,
                    Daniele
                (B) TITLE: Selective Depletion in HIV Infection
                    of T Cells That Bear Specific T Cell Receptor Vb Sequences
                (C) JOURNAL: Science
                (D) VOLUME: 254
                (E) ISSUE: 5033
                (F) PAGES: 860-862
                (J) PUBLICATION DATE: November 8, 1991

( x i ) SEQUENCE DESCRIPTION: SEQ ID NO: 21:

GATGAGTCAG GAATGCCAAA GGAA 24

( 2 ) INFORMATION FOR SEQ ID NO: 22:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini, Alessandra; Bettinardi, Alessandra; Puoti, Massimo; Primi, Daniele
        ( B ) TITLE: Selective Depletion in HIV Infection of T Cells That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 22:

CAATGCCCCA AGAACTCACC CTGC 24

( 2 ) INFORMATION FOR SEQ ID NO: 23:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini, Alessandra; Bettinardi, Alessandra; Puoti, Massimo; Primi, Daniele
        ( B ) TITLE: Selective Depletion in HIV Infection of T Cells That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 23:

AGCTCTGAGG TGCCCCAGAA TCTC 24

( 2 ) INFORMATION FOR SEQ ID NO: 24:

( i ) SEQUENCE CHARACTERISTICS:
        ( A ) LENGTH: 24 bases
        ( B ) TYPE: Nucleic Acid
        ( C ) STRANDEDNESS: Single (D) TOPOLOGY: Linear (ii) MOLECULE TYPE: Other nucleic acid
          (oligonucleotide useful in amplification of T Cell Receptor Vb region)

(iii) HYPOTHETICAL: No (vi) ORIGINAL SOURCE: Synthesized using oligonucleotide synthesis machine (xi) SEQUENCE DESCRIPTION: SEQ ID NO: 24:

TTCTGCAGAG AGGCTCAAAG GACT 24

(2) INFORMATION FOR SEQ ID NO: 25:

(i) SEQUENCE CHARACTERISTICS:
          (A) LENGTH: 24 bases
          (B) TYPE: Nucleic Acid
          (C) STRANDEDNESS: Single
          (D) TOPOLOGY: Linear (ii) MOLECULE TYPE: Other nucleic acid
          (oligonucleotide useful in amplification of T Cell Receptor Vb region)

(iii) HYPOTHETICAL: No (vi) ORIGINAL SOURCE: Synthesized using oligonucleotide synthesis machine (xi) SEQUENCE DESCRIPTION: SEQ ID NO: 25:

CTCAGTTGAA AGGCCTGATG GATC 24

(2) INFORMATION FOR SEQ ID NO: 26:

(i) SEQUENCE CHARACTERISTICS:
          (A) LENGTH: 24 bases
          (B) TYPE: Nucleic Acid
          (C) STRANDEDNESS: Single
          (D) TOPOLOGY: Linear (ii) MOLECULE TYPE: Other nucleic acid
          (oligonucleotide useful in amplification of T Cell Receptor Vb region)

(iii) HYPOTHETICAL: No (vi) ORIGINAL SOURCE: Synthesized using oligonucleotide synthesis machine (xi) SEQUENCE DESCRIPTION: SEQ ID NO: 26:

CTCAGCTCAA CAGTTCAGTG ACTA 24

(2) INFORMATION FOR SEQ ID NO: 27:

(i) SEQUENCE CHARACTERISTICS:
          (A) LENGTH: 24 bases
          (B) TYPE: Nucleic Acid
          (C) STRANDEDNESS: Single
          (D) TOPOLOGY: Linear (ii) MOLECULE TYPE: Other nucleic acid
          (oligonucleotide useful in amplification of T Cell Receptor Vb region)

(iii) HYPOTHETICAL: No (vi) ORIGINAL SOURCE: Synthesized using oligonucleotide synthesis machine (xi) SEQUENCE DESCRIPTION: SEQ ID NO: 27:

CCAATCCAGG AGGCCGAACA CTTC 24

( 2 ) INFORMATION FOR SEQ ID NO: 28:

( i ) SEQUENCE CHARACTERISTICS:
        ( A ) LENGTH:20 amino acids
        ( B ) TYPE:amino acid
        ( D ) TOPOLOGY:linear ( i i ) MOLECULE TYPE:
        ( A ) DESCRIPTION: peptide ( v i i ) IMMEDIATE SOURCE: Chemical Synthesis ( x i ) SEQUENCE DESCRIPTION: SEQ ID NO: 28:

Ser Ala Val Ile Ser Gln Lys Pro Ser Arg
                  5                     10

Asp Ile Cys Gln Arg Gly Thr Ser Leu Thr
                15                   20

( 2 ) INFORMATION FOR SEQ ID NO: 29:

( i ) SEQUENCE CHARACTERISTICS:
        ( A ) LENGTH:17 amino acids
        ( B ) TYPE:amino acid
        ( D ) TOPOLOGY:linear ( i i ) MOLECULE TYPE:
        ( A ) DESCRIPTION:peptide ( v i i ) IMMEDIATE SOURCE:Chemical Synthesis ( x i ) SEQUENCE DESCRIPTION: SEQ ID NO: 29:

Gln Leu Gln Glu Thr Glu Asn His Lys Lys
                 5                    10

Arg Phe Ser Ser Gln Cys Pro
              15

( 2 ) INFORMATION FOR SEQ ID NO: 30:

( i ) SEQUENCE CHARACTERISTICS:
        ( A ) LENGTH:18 amino acids
        ( B ) TYPE:amino acid
        ( D ) TOPOLOGY:linear ( i i ) MOLECULE TYPE:
        ( A ) DESCRIPTION:peptide ( v i i ) IMMEDIATE SOURCE:Chemical Synthesis ( x i ) SEQUENCE DESCRIPTION: SEQ ID NO: 30:

Gln Asn Leu Ser Ala Ser Arg Pro Gln Asp
                 5                    10

Arg Gln Phe Ile Leu Ser Ser Lys
              15

( 2 ) INFORMATION FOR SEQ ID NO: 31:

( i ) SEQUENCE CHARACTERISTICS:
        ( A ) LENGTH:15 amino acids
        ( B ) TYPE:amino acid
        ( D ) TOPOLOGY:linear ( i i ) MOLECULE TYPE:
        ( A ) DESCRIPTION:peptide ( v i i ) IMMEDIATE SOURCE:Chemical Synthesis ( x i ) SEQUENCE DESCRIPTION: SEQ ID NO: 31:

Asp Gly Tyr Ser Val Ser Arg Ser Lys Thr

```
                                 5            1 0
Glu  Asp  Phe  Leu  Leu
                   1 5
```

( 2 ) INFORMATION FOR SEQ ID NO: 32:

( i ) SEQUENCE CHARACTERISTICS:
        ( A ) LENGTH:16 amino acids
        ( B ) TYPE:amino acid
        ( D ) TOPOLOGY:linear ( i i ) MOLECULE TYPE:
        ( A ) DESCRIPTION:peptide ( v i i ) IMMEDIATE SOURCE:Chemical Synthesis ( x i ) SEQUENCE DESCRIPTION: SEQ ID NO: 32:

```
Pro  Arg  Asn  Arg  Ile  Thr  Lys  Ile  Gly  Lys
                   5                         1 0
Arg  Ile  Met  Leu  Glu  Cys
                   1 5
```

( 2 ) INFORMATION FOR SEQ ID NO: 33:

( i ) SEQUENCE CHARACTERISTICS:
        ( A ) LENGTH:16 amino acids
        ( B ) TYPE:amino acid
        ( D ) TOPOLOGY:linear ( i i ) MOLECULE TYPE:
        ( A ) DESCRIPTION:peptide ( v i i ) IMMEDIATE SOURCE:Chemical Synthesis ( x i ) SEQUENCE DESCRIPTION: SEQ ID NO: 33:

```
Pro  Arg  His  Leu  Val  Arg  Arg  Arg  Gly  Gln
                   5                         1 0
Glu  Ala  Arg  Leu  Arg  Cys
                   1 5
```

( 2 ) INFORMATION FOR SEQ ID NO: 34:

( i ) SEQUENCE CHARACTERISTICS:
        ( A ) LENGTH: 23 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using
        oligonucleotide synthesis machine ( x ) PUBLICATION INFORMATION:
        ( A ) AUTHORS: Imberti, Luisa; Sottini,
            Alessandra; Bettinardi, Alessandra; Puoti, Massimo; Primi,
            Daniele
        ( B ) TITLE: Selective Depletion in HIV Infection of T Cells
            That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 34:

```
GTCCTGTGTT  TGAGCCATCA  GAA                                                               2 3
```

( 2 ) INFORMATION FOR SEQ ID NO: 35:

( i ) SEQUENCE CHARACTERISTICS:
        ( A ) LENGTH: 30 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Vb region)

( i i i ) HYPOTHETICAL: No ( v ) ORIGINAL SOURCE: Synthesized using oligonucleotide synthesis machine ( x i ) SEQUENCE DESCRIPTION: SEQ ID NO: 35:

ACCCAAAAGG CCACACTGGT GTGCCTGGCC    30

( 2 ) INFORMATION FOR SEQ ID NO: 36:

( i ) SEQUENCE CHARACTERISTICS:
        ( A ) LENGTH: 18 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Va region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini,
            Alessandra; Bettinardi, Alessandra; Puoti, Massimo; Primi, Daniele
        ( B ) TITLE: Selective Depletion in HIV Infection of T Cells
            That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 36:

CTGAGGTGCA ACTACTCA    18

( 2 ) INFORMATION FOR SEQ ID NO: 37:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Va region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini,
            Alessandra; Bettinardi, Alessandra; Puoti, Massimo; Primi, Daniele
        ( B ) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 37:

AGAGGGAGCC TTAGCCTCTC TCAA 24

(2) INFORMATION FOR SEQ ID NO: 38:

(i) SEQUENCE CHARACTERISTICS:
(A) LENGTH: 24 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi, Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 38:

AATGCCACCA TGAACTGCAG TTAC 24

(2) INFORMATION FOR SEQ ID NO: 39:

(i) SEQUENCE CHARACTERISTICS:
(A) LENGTH: 21 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi, Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 39:

ACAAGCATTA CTGTACTCCT A 21

( 2 ) INFORMATION FOR SEQ ID NO: 40:

( i ) SEQUENCE CHARACTERISTICS:
        ( A ) LENGTH: 18 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Va region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini, Alessandra; Bettinardi, Alessandra; Puoti, Massimo; Primi, Daniele
        ( B ) TITLE: Selective Depletion in HIV Infection of T Cells That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 40:

GGCCCTGAAC ATTCAGGA                                                                                     18

( 2 ) INFORMATION FOR SEQ ID NO: 41:

( i ) SEQUENCE CHARACTERISTICS:
        ( A ) LENGTH: 24 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Va region)

( i i i ) HYPOTHETICAL: No ( v ) ORIGINAL SOURCE: Synthesized using oligonucleotide synthesis machine ( x ) PUBLICATION INFORMATION:
        ( A ) AUTHORS: Imberti, Luisa; Sottini, Alessandra; Bettinardi, Alessandra; Puoti, Massimo; Primi, Daniele
        ( B ) TITLE: Selective Depletion in HIV Infection of T Cells That Bear Specific T Cell Receptor Vb Sequences
        ( C ) JOURNAL: Science
        ( D ) VOLUME: 254
        ( E ) ISSUE: 5033
        ( F ) PAGES: 860-862
        ( J ) PUBLICATION DATE: November 8, 1991

( x i ) SEQUENCE DESCRIPTION: SEQ ID NO: 41:

TGACCAGCAA AATGCAACAG AAGG                                                                              24

( 2 ) INFORMATION FOR SEQ ID NO: 42:

( i ) SEQUENCE CHARACTERISTICS:
        ( A ) LENGTH: 21 bases
        ( B ) TYPE: Nucleic Acid
        ( C ) STRANDEDNESS: Single
        ( D ) TOPOLOGY: Linear ( i i ) MOLECULE TYPE: Other nucleic acid
        (oligonucleotide useful in amplification of T Cell Receptor Va region)

(  i i i ) HYPOTHETICAL: No (  v  ) ORIGINAL SOURCE: Synthesized using oligonucleotide synthesis
machine (  x  ) PUBLICATION INFORMATION:
(  A  ) AUTHORS: Imberti, Luisa; Sottini,
Alessandra; Bettinardi, Alessandra; Puoti, Massimo; Primi,
Daniele
(  B  ) TITLE: Selective Depletion in HIV Infection of T Cells
That Bear Specific T Cell Receptor Vb Sequences
(  C  ) JOURNAL: Science
(  D  ) VOLUME: 254
(  E  ) ISSUE: 5033
(  F  ) PAGES: 860-862
(  J  ) PUBLICATION DATE: November 8, 1991

(  x i  ) SEQUENCE DESCRIPTION: SEQ ID NO: 42:

AGGAGCCATT GTCCAGATAA A 21

( 2 ) INFORMATION FOR SEQ ID NO: 43:

(  i  ) SEQUENCE CHARACTERISTICS:
(  A  ) LENGTH: 24 bases
(  B  ) TYPE: Nucleic Acid
(  C  ) STRANDEDNESS: Single
(  D  ) TOPOLOGY: Linear (  i i  ) MOLECULE TYPE: Other nucleic acid
(oligonucleotide useful in amplification of T Cell Receptor Va
region)

(  i i i ) HYPOTHETICAL: No (  v  ) ORIGINAL SOURCE: Synthesized using oligonucleotide synthesis
machine (  x  ) PUBLICATION INFORMATION:
(  A  ) AUTHORS: Imberti, Luisa; Sottini,
Alessandra; Bettinardi, Alessandra; Puoti, Massimo; Primi,
Daniele
(  B  ) TITLE: Selective Depletion in HIV Infection of T Cells
That Bear Specific T Cell Receptor Vb Sequences
(  C  ) JOURNAL: Science
(  D  ) VOLUME: 254
(  E  ) ISSUE: 5033
(  F  ) PAGES: 860-862
(  J  ) PUBLICATION DATE: November 8, 1991

(  x i  ) SEQUENCE DESCRIPTION: SEQ ID NO: 43:

GCTTATTCAA ACAGCGCCTC AGAC 24

( 2 ) INFORMATION FOR SEQ ID NO: 44:

(  i  ) SEQUENCE CHARACTERISTICS:
(  A  ) LENGTH: 24 bases
(  B  ) TYPE: Nucleic Acid
(  C  ) STRANDEDNESS: Single
(  D  ) TOPOLOGY: Linear (  i i  ) MOLECULE TYPE: Other nucleic acid
(oligonucleotide useful in amplification of T Cell Receptor Va
region)

(  i i i ) HYPOTHETICAL: No (  v  ) ORIGINAL SOURCE: Synthesized using oligonucleotide synthesis
machine (  x  ) PUBLICATION INFORMATION:
(  A  ) AUTHORS: Imberti, Luisa; Sottini,
Alessandra; Bettinardi, Alessandra; Puoti, Massimo; Primi,
Daniele
(  B  ) TITLE: Selective Depletion in HIV Infection of T Cells
That Bear Specific T Cell Receptor Vb Sequences
(  C  ) JOURNAL: Science (D) VOLUME: 254
(E) ISSUE: 5033
(F) PAGES: 860-862
(J) PUBLICATION DATE: November 8, 1991

(xi) SEQUENCE DESCRIPTION: SEQ ID NO: 44:

CAGAGAGTGA CTCAGCCCGA GAAG 24

(2) INFORMATION FOR SEQ ID NO: 45:

(i) SEQUENCE CHARACTERISTICS:
(A) LENGTH: 24 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 45:

ACCCAGCTGG TGGAGCAGAG CCCT 24

(2) INFORMATION FOR SEQ ID NO: 46:

(i) SEQUENCE CHARACTERISTICS:
(A) LENGTH: 21 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi, Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 46:

AGAAAGCAAG GACCAAGTGT T 21

(2) INFORMATION FOR SEQ ID NO: 47:

(i) SEQUENCE CHARACTERISTICS:
    (A) LENGTH: 24 bases
    (B) TYPE: Nucleic Acid
    (C) STRANDEDNESS: Single
    (D) TOPOLOGY: Linear (ii) MOLECULE TYPE: Other nucleic acid
    (oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
    (A) AUTHORS: Imberti, Luisa; Sottini, Alessandra; Bettinardi, Alessandra; Puoti, Massimo; Primi, Daniele
    (B) TITLE: Selective Depletion in HIV Infection of T Cells That Bear Specific T Cell Receptor Vb Sequences
    (C) JOURNAL: Science
    (D) VOLUME: 254
    (E) ISSUE: 5033
    (F) PAGES: 860-862
    (J) PUBLICATION DATE: November 8, 1991

(xi) SEQUENCE DESCRIPTION: SEQ ID NO: 47:

CACAACCTAA CTCAAGCGCA GACT                                24

(2) INFORMATION FOR SEQ ID NO: 48:

(i) SEQUENCE CHARACTERISTICS:
    (A) LENGTH: 24 bases
    (B) TYPE: Nucleic Acid
    (C) STRANDEDNESS: Single
    (D) TOPOLOGY: Linear (ii) MOLECULE TYPE: Other nucleic acid
    (oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
    (A) AUTHORS: Imberti, Luisa; Sottini, Alessandra; Bettinardi, Alessandra; Puoti, Massimo; Primi, Daniele
    (B) TITLE: Selective Depletion in HIV Infection of T Cells That Bear Specific T Cell Receptor Vb Sequences
    (C) JOURNAL: Science
    (D) VOLUME: 254
    (E) ISSUE: 5033
    (F) PAGES: 860-862
    (J) PUBLICATION DATE: November 8, 1991

(xi) SEQUENCE DESCRIPTION: SEQ ID NO: 48:

CTCATCAACC TGTTTTACAT TCCC                                24

(2) INFORMATION FOR SEQ ID NO: 49:

(i) SEQUENCE CHARACTERISTICS:
    (A) LENGTH: 20 bases
    (B) TYPE: Nucleic Acid
    (C) STRANDEDNESS: Single
    (D) TOPOLOGY: Linear (ii) MOLECULE TYPE: Other nucleic acid
    (oligonucleotide useful in amplification of T Cell Receptor Va region)

(iii) HYPOTHETICAL: No ( v ) ORIGINAL SOURCE: Synthesized using oligonucleotide synthesis
machine ( x ) PUBLICATION INFORMATION:
( A ) AUTHORS: Imberti, Luisa; Sottini,
Alessandra; Bettinardi, Alessandra; Puoti, Massimo; Primi,
Daniele
( B ) TITLE: Selective Depletion in HIV Infection of T Cells
That Bear Specific T Cell Receptor Vb Sequences
( C ) JOURNAL: Science
( D ) VOLUME: 254
( E ) ISSUE: 5033
( F ) PAGES: 860-862
( J ) PUBLICATION DATE: November 8, 1991

( x i ) SEQUENCE DESCRIPTION: SEQ ID NO: 49:

GCAGCTTCCC TTCCAGCAAT 20

( 2 ) INFORMATION FOR SEQ ID NO: 50:

( i ) SEQUENCE CHARACTERISTICS:
( A ) LENGTH: 20 bases
( B ) TYPE: Nucleic Acid
( C ) STRANDEDNESS: Single
( D ) TOPOLOGY: Linear ( i i ) MOLECULE TYPE: Other nucleic acid
(oligonucleotide useful in amplification of T Cell Receptor Va region)

( i i i ) HYPOTHETICAL: No ( v ) ORIGINAL SOURCE: Synthesized using oligonucleotide synthesis
machine ( x ) PUBLICATION INFORMATION:
( A ) AUTHORS: Imberti, Luisa; Sottini,
Alessandra; Bettinardi, Alessandra; Puoti, Massimo; Primi,
Daniele
( B ) TITLE: Selective Depletion in HIV Infection of T Cells
That Bear Specific T Cell Receptor Vb Sequences
( C ) JOURNAL: Science
( D ) VOLUME: 254
( E ) ISSUE: 5033
( F ) PAGES: 860-862
( J ) PUBLICATION DATE: November 8, 1991

( x i ) SEQUENCE DESCRIPTION: SEQ ID NO: 50:

AGAACCTGAC TGCCCAGGAA 20

( 2 ) INFORMATION FOR SEQ ID NO: 51:

( i ) SEQUENCE CHARACTERISTICS:
( A ) LENGTH: 18 bases
( B ) TYPE: Nucleic Acid
( C ) STRANDEDNESS: Single
( D ) TOPOLOGY: Linear ( i i ) MOLECULE TYPE: Other nucleic acid
(oligonucleotide useful in amplification of T Cell Receptor Va region)

( i i i ) HYPOTHETICAL: No ( v ) ORIGINAL SOURCE: Synthesized using oligonucleotide synthesis
machine ( x ) PUBLICATION INFORMATION:
( A ) AUTHORS: Imberti, Luisa; Sottini,
Alessandra; Bettinardi, Alessandra; Puoti, Massimo; Primi,
Daniele
( B ) TITLE: Selective Depletion in HIV Infection of T Cells
That Bear Specific T Cell Receptor Vb Sequences
( C ) JOURNAL: Science
( D ) VOLUME: 254
( E ) ISSUE: 5033

(F) PAGES: 860-862
            (J) PUBLICATION DATE: November 8, 1991

(xi) SEQUENCE DESCRIPTION: SEQ ID NO: 51:

CCTCCAGTTC CTTCTGAA                                                                                                  18

(2) INFORMATION FOR SEQ ID NO: 52:

(i) SEQUENCE CHARACTERISTICS:
            (A) LENGTH: 24 bases
            (B) TYPE: Nucleic Acid
            (C) STRANDEDNESS: Single
            (D) TOPOLOGY: Linear (ii) MOLECULE TYPE: Other nucleic acid
            (oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
            (A) AUTHORS: Imberti, Luisa; Sottini, Alessandra; Bettinardi, Alessandra; Puoti, Massimo; Primi, Daniele
            (B) TITLE: Selective Depletion in HIV Infection of T Cells That Bear Specific T Cell Receptor Vb Sequences
            (C) JOURNAL: Science
            (D) VOLUME: 254
            (E) ISSUE: 5033
            (F) PAGES: 860-862
            (J) PUBLICATION DATE: November 8, 1991

(xi) SEQUENCE DESCRIPTION: SEQ ID NO: 52:

CAGCAGGTGA AACAAAGTCC TCAA                                                                                           24

(2) INFORMATION FOR SEQ ID NO: 53:

(i) SEQUENCE CHARACTERISTICS:
            (A) LENGTH: 18 bases
            (B) TYPE: Nucleic Acid
            (C) STRANDEDNESS: Single
            (D) TOPOLOGY: Linear (ii) MOLECULE TYPE: Other nucleic acid
            (oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
            (A) AUTHORS: Imberti, Luisa; Sottini, Alessandra; Bettinardi, Alessandra; Puoti, Massimo; Primi, Daniele
            (B) TITLE: Selective Depletion in HIV Infection of T Cells That Bear Specific T Cell Receptor Vb Sequences
            (C) JOURNAL: Science
            (D) VOLUME: 254
            (E) ISSUE: 5033
            (F) PAGES: 860-862
            (J) PUBLICATION DATE: November 8, 1991

(xi) SEQUENCE DESCRIPTION: SEQ ID NO: 53:

TGTCAGGCAA TGACAAGG                                                                                                  18

(2) INFORMATION FOR SEQ ID NO: 54:

(i) SEQUENCE CHARACTERISTICS:
            (A) LENGTH: 24 bases (B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi, Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 54:

TACACAGCCA CAGGATACCC TTCC            24

(2) INFORMATION FOR SEQ ID NO: 55:

(i) SEQUENCE CHARACTERISTICS:
(A) LENGTH: 24 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
(A) AUTHORS: Imberti, Luisa; Sottini, Alessandra; Bettinardi, Alessandra; Puoti, Massimo; Primi, Daniele
(B) TITLE: Selective Depletion in HIV Infection of T Cells That Bear Specific T Cell Receptor Vb Sequences
(C) JOURNAL: Science
(D) VOLUME: 254
(E) ISSUE: 5033
(F) PAGES: 860-862
(J) PUBLICATION DATE: November 8, 1991

(xi) SEQUENCE DESCRIPTION: SEQ ID NO: 55:

ATGTCTAGCA CAGTTTTGTC TGTG            24

(2) INFORMATION FOR SEQ ID NO: 56:

(i) SEQUENCE CHARACTERISTICS:
(A) LENGTH: 24 bases
(B) TYPE: Nucleic Acid
(C) STRANDEDNESS: Single
(D) TOPOLOGY: Linear (ii) MOLECULE TYPE: Other nucleic acid
(oligonucleotide useful in amplification of T Cell Receptor Va region)

(iii) HYPOTHETICAL: No (v) ORIGINAL SOURCE: Synthesized using oligonucleotide synthesis machine (x) PUBLICATION INFORMATION:
   (A) AUTHORS: Imberti, Luisa; Sottini,
       Alessandra; Bettinardi, Alessandra; Puoti, Massimo; Primi,
       Daniele
   (B) TITLE: Selective Depletion in HIV Infection of T Cells
       That Bear Specific T Cell Receptor Vb Sequences
   (C) JOURNAL: Science
   (D) VOLUME: 254
   (E) ISSUE: 5033
   (F) PAGES: 860-862
   (J) PUBLICATION DATE: November 8, 1991

(xi) SEQUENCE DESCRIPTION: SEQ ID NO: 56:

ATATCCAGAA CCCTGACCCT GCCG                                          24

(2) INFORMATION FOR SEQ ID NO: 57:

(i) SEQUENCE CHARACTERISTICS:
       (A) LENGTH: 30 bases
       (B) TYPE: Nucleic Acid
       (C) STRANDEDNESS: Single
       (D) TOPOLOGY: Linear (ii) MOLECULE TYPE: Other nucleic acid
        (oligonucleotide useful in amplification of T Cell Receptor Va region)

(iii) HYPOTHETICAL: No (v) ORIGINAL SOURCE: Synthesized using oligonucleotide synthesis
       machine (xi) SEQUENCE DESCRIPTION: SEQ ID NO: 57:

CAGTGACAAG TGTGTCTGCC TATTCACCGA                                    30